(12) United States Patent
Brennan et al.

(10) Patent No.: US 8,711,364 B2
(45) Date of Patent: Apr. 29, 2014

(54) OPTICAL COHERENCE TOMOGRAPHY WITH MULTIPLE SAMPLE ARMS

(75) Inventors: Jeffrey Brennan, Los Angeles, CA (US); Mark Humayun, Glendale, CA (US); Sean Caffey, Manhattan Beach, CA (US)

(73) Assignee: oProbe, LLC, Pasadena, CA (US)

( * ) Notice: Subject to any disclaimer, the term of this patent is extended or adjusted under 35 U.S.C. 154(b) by 185 days.

(21) Appl. No.: 13/106,388

(22) Filed: May 12, 2011

(65) Prior Publication Data

US 2011/0279821 A1  Nov. 17, 2011

Related U.S. Application Data

(60) Provisional application No. 61/334,364, filed on May 13, 2010.

(51) Int. Cl.
G01B 9/02 (2006.01)

(52) U.S. Cl.
USPC .......................................................... 356/479

(58) Field of Classification Search
USPC ................................................. 356/479, 497
See application file for complete search history.

(56) References Cited

U.S. PATENT DOCUMENTS

| | | | |
|---|---|---|---|
| 5,321,501 A | 6/1994 | Swanson et al. | |
| 5,459,570 A | 10/1995 | Swanson et al. | |
| 5,465,147 A | 11/1995 | Swanson | |
| 5,748,598 A | 5/1998 | Swanson et al. | |
| 5,784,352 A | 7/1998 | Swanson et al. | |
| 5,962,852 A | 10/1999 | Knuettel et al. | |
| 6,122,538 A | 9/2000 | Sliwa, Jr. et al. | |
| 6,134,003 A | 10/2000 | Tearney et al. | |
| 6,160,826 A | 12/2000 | Swanson et al. | |
| 6,421,164 B2 | 7/2002 | Tearney et al. | |
| 6,454,761 B1 | 9/2002 | Freedman | |
| 6,485,413 B1 | 11/2002 | Boppart et al. | |
| 6,498,948 B1 | 12/2002 | Ozawa et al. | |
| 6,501,551 B1 | 12/2002 | Tearney et al. | |
| 6,564,087 B1 | 5/2003 | Pitris et al. | |
| 7,261,687 B2 | 8/2007 | Yang | |
| 7,364,543 B2 | 4/2008 | Yang et al. | |
| 7,602,500 B2 * | 10/2009 | Izatt et al. | 356/497 |
| 2002/0166946 A1 | 11/2002 | Iizuka et al. | |

(Continued)

FOREIGN PATENT DOCUMENTS

| EP | 1447049 | 8/2004 |
|---|---|---|
| EP | 1447049 A1 | 8/2004 |

(Continued)

OTHER PUBLICATIONS

International Search Report and Written Opinion mailed Feb. 3, 2012 for International Application No. PCT/US2011/036195 (29 pages).

(Continued)

*Primary Examiner* — Tarifur Chowdhury
*Assistant Examiner* — Jonathan Hansen
(74) *Attorney, Agent, or Firm* — Bingham McCutchen LLP

(57) ABSTRACT

A multiplexed OCT imaging system includes a plurality of sample arms, an imaging engine, and an optical controller. The sample arms are optically coupled to the imaging engine via the optical controller; the optical controller multiplexes optical signals from the sample arms to permit some of the sample arms to operate sequentially or simultaneously.

18 Claims, 28 Drawing Sheets

(56) References Cited

U.S. PATENT DOCUMENTS

| | | |
|---|---|---|
| 2003/0142934 A1 | 7/2003 | Pan et al. |
| 2005/0182329 A1 | 8/2005 | Ostrovsky |
| 2006/0103850 A1 | 5/2006 | Alphonse et al. |
| 2006/0132790 A1 | 6/2006 | Gutin |
| 2006/0142657 A1 | 6/2006 | Quaid et al. |
| 2006/0293563 A1 | 12/2006 | Banik et al. |
| 2007/0038119 A1 | 2/2007 | Chen et al. |
| 2007/0167678 A1 | 7/2007 | Moskowitz et al. |
| 2007/0208400 A1 | 9/2007 | Nadkarni et al. |
| 2007/0278389 A1 | 12/2007 | Ajgaonkar et al. |
| 2008/0051629 A1 | 2/2008 | Sugiyama et al. |
| 2008/0146941 A1 | 6/2008 | Dala-Krishna |
| 2008/0181358 A1 | 7/2008 | Van Kampen et al. |
| 2008/0304123 A1 | 12/2008 | Wang et al. |
| 2008/0304144 A1 | 12/2008 | Reimer et al. |
| 2009/0177094 A1* | 7/2009 | Brown et al. ............... 600/476 |
| 2010/0041986 A1 | 2/2010 | Nguyen et al. |
| 2010/0228119 A1 | 9/2010 | Brennan et al. |
| 2010/0228123 A1 | 9/2010 | Brennan et al. |
| 2010/0228124 A1 | 9/2010 | Brennan et al. |
| 2010/0228132 A1 | 9/2010 | Brennan et al. |
| 2010/0228238 A1 | 9/2010 | Brennan et al. |
| 2012/0026463 A1* | 2/2012 | Makihira et al. ............ 351/206 |
| 2013/0010262 A1* | 1/2013 | Sato et al. .................... 351/206 |

FOREIGN PATENT DOCUMENTS

| | | |
|---|---|---|
| EP | 1839561 | 10/2007 |
| EP | 2090223 | 8/2009 |
| EP | 2090223 A1 | 8/2009 |
| FR | 2899089 | 10/2007 |
| FR | 2899089 A1 | 10/2007 |
| WO | WO-99/049780 | 10/1999 |
| WO | WO-99/49780 A1 | 10/1999 |
| WO | WO-00/42906 | 7/2000 |
| WO | WO-03/071223 | 8/2003 |
| WO | WO-03/071223 A2 | 8/2003 |
| WO | WO-2006/054975 | 5/2006 |
| WO | WO-2006/054975 A1 | 5/2006 |
| WO | WO-2007/038682 | 4/2007 |
| WO | WO-2007/103721 | 9/2007 |
| WO | WO-2008/115060 | 9/2008 |
| WO | WO-2008/115060 A1 | 9/2008 |
| WO | WO-2008/153999 | 12/2008 |
| WO | WO-2010/104752 | 9/2010 |

OTHER PUBLICATIONS

Invitation to Pay Additional Fees and Partial Search Report mailed Feb. 6, 2012 for International Application No. PCT/US2011/052873 (5 pages).

Invitation to Pay Additional Fees and Partial Search Report mailed Nov. 22, 2010 for International Application No. PCT/US2010/026293 (6 pages).

International Search Report and Written Opinion mailed Jul. 1, 2011 for International Application No. PCT/US2010/026293 (22 pages).

International Preliminary Report on Patentability mailed Sep. 22, 2011 for International Application No. PCT/US2010/026293 (16 pages).

Invitation to Pay Additional Fees and Partial Search Report mailed Oct. 5, 2011 for International Application No. PCT/US2011/036195 (5 pages).

International Search Report and Written Opinion mailed Dec. 20, 2011 for International Application No. PCT/US2011/036196 (14 pages).

International Preliminary Report on Patentability and Written Opinion for International Application No. PCT/US2011/036195, issued Nov. 13, 2012.

International Search Report issued for International Application No. PCT/US2011/036195, completed Jan. 23, 2013 and mailed Feb. 2, 2012.

International Search Report and Written Opinion mailed Apr. 4, 2012 for International Application No. PCT/US2011/052873 (17 pages).

* cited by examiner

OPTICAL COHERENCE TOMOGRAPHY WITH MULTIPLE SAMPLE ARMS

CROSS-REFERENCE TO RELATED APPLICATIONS

This application claims priority to and the benefit of, and incorporates herein by reference in their entireties, U.S. Provisional Patent Application No. 61/334,364, which was filed on May 13, 2010, the entire disclosure of which is hereby incorporated by reference.

TECHNICAL FIELD

In various embodiments, the present invention relates generally to optical coherence tomography (OCT) imaging systems for use in various medical and veterinary applications.

BACKGROUND

Advances in the development of novel diagnostic techniques—including new or improved imaging modalities—provide surgeons with more information and a better understanding of the area being treated. This enables surgeon to collect, for example, real-time and non-destructive biopsies including analysis of regions that are typically difficult to access. These innovations have resulted in significant improvements in diagnostic evaluation, treatment options, and patient outcomes for a variety of maladies.

One such useful diagnostic technique is optical coherence tomography (OCT), an interferometric technique utilizing light (typically infrared) for noninvasive diagnosis and imaging. OCT is used to obtain sub-surface images of translucent or opaque materials at a resolution equivalent to a low-power microscope. OCT provides tissue morphology imagery at much higher resolution (better than 10 µm) than other imaging modalities such as MRI or ultrasound. OCT has transformed the field of ophthalmology and promises to have a similar impact on a variety of other medical specialties. A particular mode of OCT, termed "A-scan," provides one-dimensional axial depth scans of the tissue of interest, thus providing information on the identity, size, and depth of sub-surface features. A series of spatially adjacent A-scans (typically lying in a straight line) may be combined to form a two-dimensional reconstructed image of the imaged area (termed a "B-scan"), offering surgeons a visual reconstruction of subsurface features. Likewise, three-dimensional (3D) images, termed "C-scans," may be formed by "stacking" multiple B-scans.

OCT systems have become a mainstay in hospitals and ophthalmology clinics for diagnostic evaluation and imaging purposes. Despite the clear benefit of the technology to the health and treatment of the patient, the cost of an OCT system often prohibits hospitals and clinics from purchasing a sufficient number of OCT systems to accommodate patient demand. This resource limitation creates a bottleneck that complicates the examination process, slows patient throughput, and ultimately reduces the productivity of the medical staff.

Consequently, there is an urgent need for OCT systems that can handle multiple patients simultaneously or nearly so, thereby reducing costs and increasing patient throughput.

SUMMARY

In various embodiments, the present invention relates to OCT systems and methods for performing multiple scans in a multiplexed fashion. Such OCT systems and methods may sequentially or simultaneously generate images of the multiple targets through information collected from the sample arms. The invention thereby permits high patient throughput by permitting treatment using multiple OCT probes whose outputs are handled simultaneously or sequentially. In various embodiments, sequential handling of OCT output occurs quickly enough that each clinician using an OCT probe does not experience significant delay.

Accordingly, in one aspect, the invention pertains to a multiplexed OCT imaging system comprising a plurality of sample arms (i.e., OCT probes), at least one imaging engine, and an optical controller. In various embodiments, the sample arms are optically coupled to the imaging engine(s) via the optical controller, which multiplexes optical signals from the sample arms to permit at least some of them to operate sequentially or simultaneously. In some embodiments, the sample arms comprise optical fibers for transmitting light between the at least one imaging engine and a plurality of targets. For example, the optical fibers may be single-mode optical fibers.

In some embodiments, the system comprises display hardware associated with each sample arm to display images of the target of interest. In various implementations, the display hardware connects to the imaging engine(s) directly or via a local area network.

In some embodiments, the imaging engine(s) comprise(s) a reference arm for generating an interference pattern with respect to the radiation from the sample arm. This interference pattern results from the difference in optical path-length or phase between the reference arm and the sample arm and encodes the depth information. In various embodiments, a mechanical element is included to adjust the relative position between the reference arm and the sample arm. Alternatively, an optical component may be included to auto-match the optical path-lengths between the reference arm and the sample arm. The sample arm and reference arm may share a common beam path with respect to a target.

In some embodiments, the optical controller, for example, may be an optical switch, a time-division multiplexer, or a wavelength-division multiplexer; the wavelength-division multiplexer may comprise interference or thin film filters for avoiding overlapping wavelengths between each sample arm.

The optical controller may activate a new imaging engine upon detecting a new sample arm; such activation may occur upon the detection of a demand issued by a user. For example, the optical controller may be a switch matrix that balances loads among activated imaging engines in order to minimize the number of image-engine activations.

In some embodiments, the imaging engine(s) of the system comprise(s) a broadband light source and a spectrometer-based OCT interferometer to separate different bands of the broadband light within the sample arms.

In a second aspect, the invention relates to a method of using a multiplexed OCT imaging system to provide a plurality of images. In various embodiments, the method comprises emitting light from each of a plurality of light sources upon one of a plurality of targets and collecting reflected light from each target, and sequentially or simultaneously generating OCT images. Each image is associated with one of the plurality of targets based on the reflected light.

In some embodiments, the method further comprises emitting reference light from the light source upon a reference plane, and generating OCT images comprises processing and reconstructing interference patterns between the reflected light from each target and reflected light from the reference plane. In various implementations, light is emitted onto the targets sequentially and/or simultaneously to produce a plurality of OCT signals, which are multiplexed. The multiplexing may be, for example, wavelength-division multiplexing or time-division multiplexing.

These and other objects, along with advantages and features of the present invention herein disclosed, will become more apparent through reference to the following description, the accompanying drawings, and the claims. Furthermore, it is to be understood that the features of the various embodiments described herein are not mutually exclusive and can exist in various combinations and permutations.

BRIEF DESCRIPTION OF THE DRAWINGS

In the drawings, like reference characters generally refer to the same parts throughout the different views. Also, the drawings are not necessarily to scale, with an emphasis instead generally being placed upon illustrating the principles of the invention. In the following description, various embodiments of the present invention are described with reference to the following drawings, in which.

DETAILED DESCRIPTION

Figure 1:
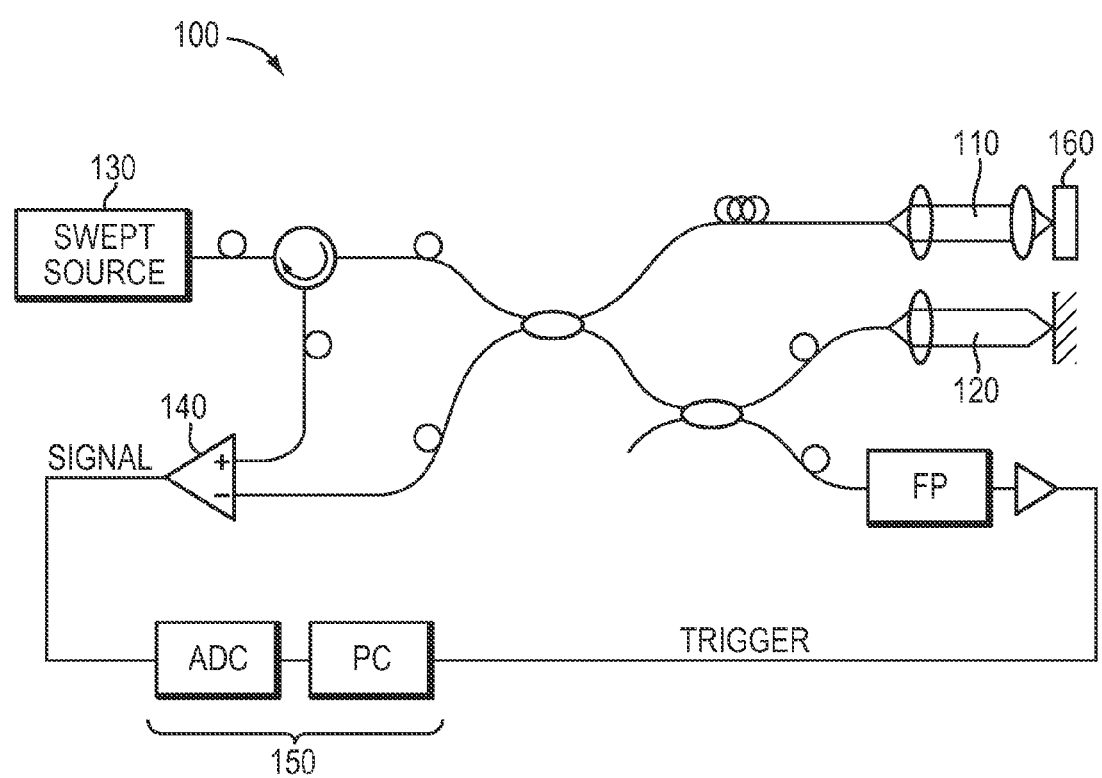
FIG. 1 schematically depicts components of an OCT interferometry system utilizing a swept-source light source, an interferometer, a sample arm, a balanced photodetector, and data acquisition and processing hardware.

Optical coherence tomography (OCT) is an imaging methodology that provides three-dimensional images of biological tissues at sub-micrometer lateral and axial resolution. The advantages of OCT include high imaging resolution, real-time imaging, non-invasiveness, and compact size. FIG. 1 depicts an exemplary OCT interferometry system 100 in accordance with embodiments of the present invention, although alternative systems with similar functionality are also within the scope of the invention. As depicted, OCT interferometry system 100 includes a sample arm 110, a reference arm 120, a light source 130, a photodetector 140, and data-acquisition and processing hardware (or a "driver") 150. Light from light source 130 (which may be, e.g., a swept-source or tunable laser) travels through optical fibers to sample arm 110 and reference arm 120. Via sample arm 110, the light illuminates a sample of interest 160, which may include or consist essentially of, e.g., biological tissue. In a typical medical imaging application, the sample arm is the only component of the OCT imaging system that requires contact with or close proximity to the area to be imaged (e.g., the eye). Various features of interest of sample 160 reflect the light in different amounts or from different depths. The reflected light is combined with light reflected by reference arm 120 (which typically includes or consists essentially of a mirror), and the interference pattern thus generated provides information about the spatial dimensions and location of structures within sample 160. In OCT, an optical interferometer is used to detect the reflected coherent light. Most light illuminating the sample is scattered and no longer coherent with the light emitted from the light source; therefore, the scattered light can be effectively filtered out by the interferometer. On the other hand, light reflected by structures in the sample remains coherent with the light emitted from the light source and can thus be detected and processed to create an OCT image.

Hardware 150 may be a personal-computer- (PC-) based architecture, and may include a high-speed analog-to-digital converter (for example, on a PCI bus) that digitizes the output of photodetector 140 at a sampling rate ranging from several million samples per second to several billion samples per second. In an embodiment, the digitized data is processed by the PC processor and readily available or straightforwardly implemented by software that, e.g., performs a Fourier transform and signal processing and reconstruction algorithms on the data. In another embodiment the data processing is performed in dedicated hardware, e.g., an ASIC, FPGA, DSP, or combination of these devices. The hardware and/or associated software derives, e.g., reconstructed images, biometric measurements, and/or quantitative data from the data produced by OCT interferometry system 100.

Distributed OCT

Embodiments of the present invention provide a distributed OCT imaging system utilizing a sample arm separated from a remotely-located imaging engine, where the imaging engine includes one or more of the following: a light source (e.g., a swept-source laser or a super-luminescent light-emitting diode), an interferometer (containing various optical components therein), a reference arm, data-acquisition hardware, signal-processing hardware, and/or display hardware (e.g., an LCD and driver). In other words, some or all of these components may be located remotely from the sample arm, but depending on the design and application, one or more of these components may be co-located with the sample arm.

Figure 2:
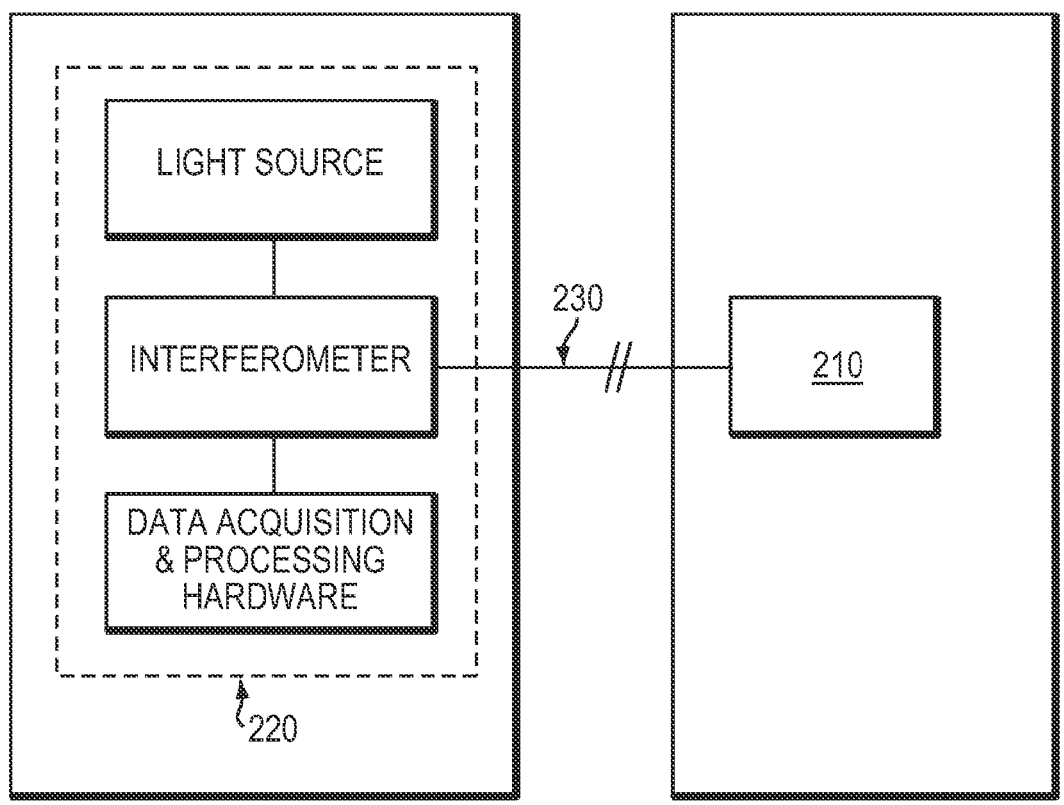
FIG. 2 schematically depicts an OCT interferometry system incorporating an OCT imaging engine and a remotely-located sample arm.

The data-acquisition hardware and electronic-processing hardware may be implemented utilizing off the-shelf-hardware such as a PC, or they may be implemented in dedicated hardware, such as an application-specific integrated circuit (ASIC), field-programmable gate array (FPGA), digital signal processor (DSP), graphical processing unit (GPU), or combination of these devices. FIG. 2 depicts a sample arm 210 connected to a remotely-located OCT imaging engine 220 by a length of optical fiber 230, preferably a single-mode optical fiber. The separation distance between the imaging engine 220 and the sample arm 210 may vary and depends on the particular application. For example, in some facilities the imaging engine and the sample arm may be located in adjacent rooms, while in other facilities these will be located on different floors or even different buildings. Utilizing a single-mode fiber, separation distances of several hundred meters or more are possible. For example, the sample arm 210 may be located in an examination room of a doctor's clinic, while the imaging engine 220 may be placed in another location (e.g., a server room in the same building or an adjacent one), with the two linked by an optical fiber 230, preferably single-mode to decrease dispersive effects. Depending on the configuration, the imaging engine may constitute the majority of bulk, weight, and noise (e.g., from fans cooling the electronics) of the system, and it therefore may be preferable to locate the imaging engine or portions thereof in a more convenient or less conspicuous location. Furthermore, locating the bulk of the OCT hardware in another location may assist in maintaining a sterile field. The imaging engine may be linked (e.g., via a wired or wireless computer network) to a low-cost multi-purpose PC or alternate display technology in the examination room for OCT imaging display purposes.

Figure 3A:
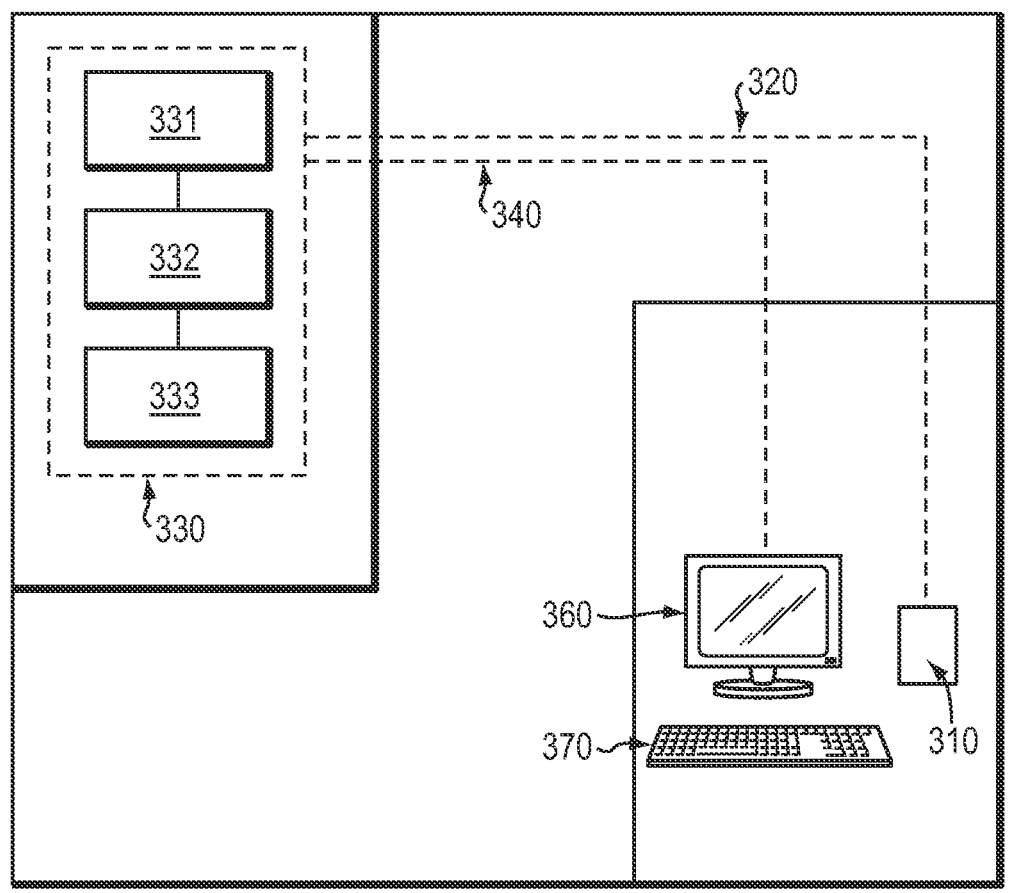
FIGS. 3A and 3B schematically depict an OCT imaging system with the imaging engine and the sample arm located in separate rooms and with display and control interface available associated with the sample arm via direct point-to-point electrical connections and/or a local area network.
Figure 3B:
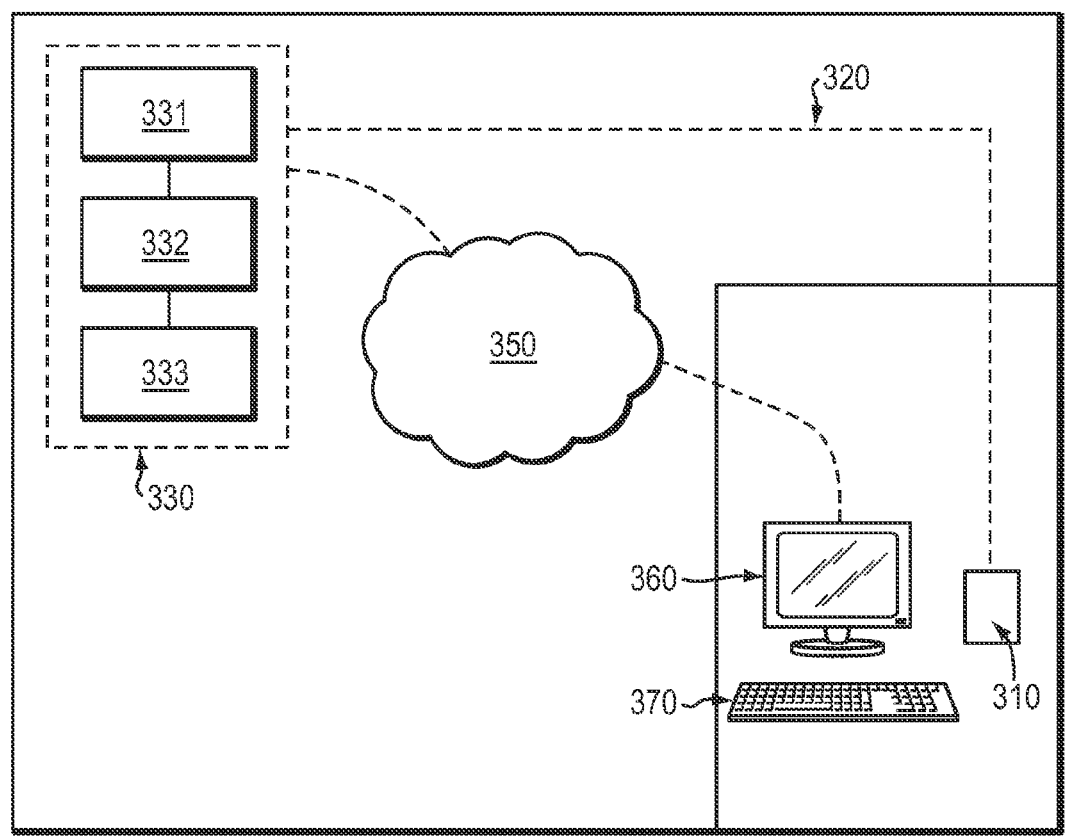

Furthermore, the components that constitute the imaging engine may be distributed across multiple locations. For example, with reference to FIGS. 3A and 3B, the sample arm 310 may be located in the examination room and linked via optical fiber 320 to the light source 331, interferometer 332, and data-acquisition and processing hardware 333 located in a second location, which is electrically linked (e.g., via a direct point-to-point connection 340 or via a wired or wireless network, such as Ethernet 350) to image-display hardware 360 and control interface 370 located in the same examination room as the sample arm. In another embodiment, the image-display hardware 360 and control interface 370 are located in a separate third location.

Multiple Sample Arm OCT

Figure 4A:
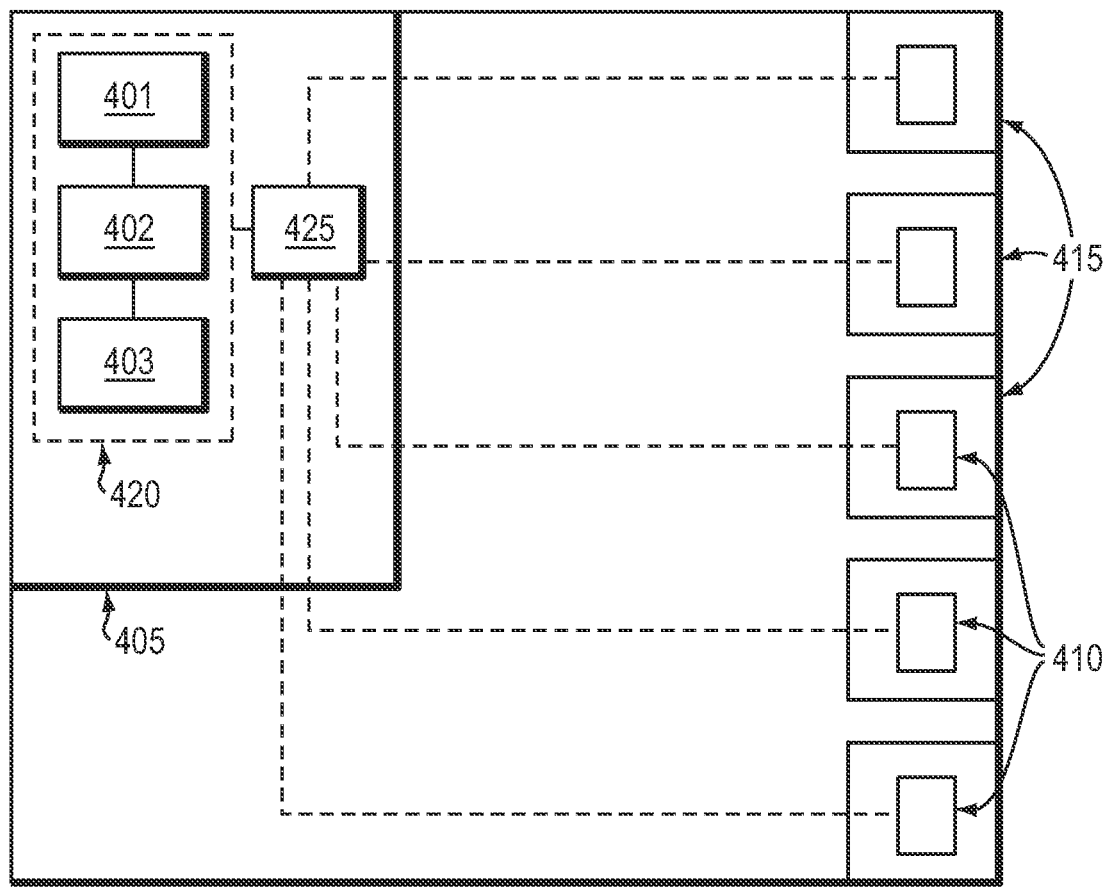
FIG. 4A schematically illustrates an OCT imaging system with multiple sample arms installed with the imaging engine via an optical controller. Each of the sample arms are located in different rooms, separate from the imaging engine.

Embodiments of the present invention provide an OCT imaging system utilizing an interferometer with one or more sample arms each including an optical assembly appropriate for the intended application. In one embodiment, as illustrated in FIG. 4A, the light source 401, interferometer 402, and related data-acquisition and processing equipment 403 are located in a central area or room 405 and each of the multiple sample arms 410 is located in a separate area 415. For example, each sample arm may be located in a separate examination room outside area 405, but each sample arm is linked to the same remotely-located OCT imaging engine 420. In another embodiment, the multiple sample arms are located in the same examination room. The multiple sample arms may be interfaced to the interferometer via an optical controller 425.

In one embodiment, the optical controller 425 (e.g., a wavelength-division multiplexer, a time-division multiplexer, or an optical switch) multiplexes optical signals from the sample arms to permit at least some of the sample arms to operate substantially simultaneously and enables a doctor, clinician, or even automated software to select which sample arm (i.e., which examination room) is optically linked to the centralized imaging engine. (By "substantially simultaneously" is meant, in this context, that users of the sample arms do not experience clinically significant latency, jitter or delay in the operation of the sample arm that interferes with their ability to conduct an examination.) A wavelength-division multiplexer (WDM) joins optical signals together, i.e., it multiplexes multiple optical signals of different wavelengths from the sample arms onto a single optical fiber connected to the imaging engine. The wavelengths of the multiplexed signals are band-separated sufficiently to avoid interference or crosstalk. In time-division multiplexing (TDM), two or more signals are transferred in an optical fiber, but are partitioned among timeslices; that is, the signals physically "take turns" on a divided time domain of the signal channel. Both WDM and TDM enable multiplication of optical fiber capacity for transmitting optical signals from sample arms simultaneously to one or more imaging engines, and thus it is not necessary to optically switch the sample arms into and out of the system.

As noted below, depending on the implementation, the amount of time required to obtain an image with a sample arm—i.e., the duration of the communication between the sample arm and the imaging engine—may be small, i.e., on the order of seconds. Moreover, most of the time involved in capturing an image is expended in positioning and preparing the patient. As a result, operational simultaneity among sample arms and true multiplexing may not be necessary as a practical matter. Optical controller 425 may simply accord the various sample arms access to a single imaging engine 420 on a sequential basis, or invoke additional image-processing applications and balance loads as needed. So long as no clinician experiences excessive delays, relatively inexpensive systems configured for sequential operation can be employed, and this operation may be substantially simultaneous as understood herein.

Figure 4B:
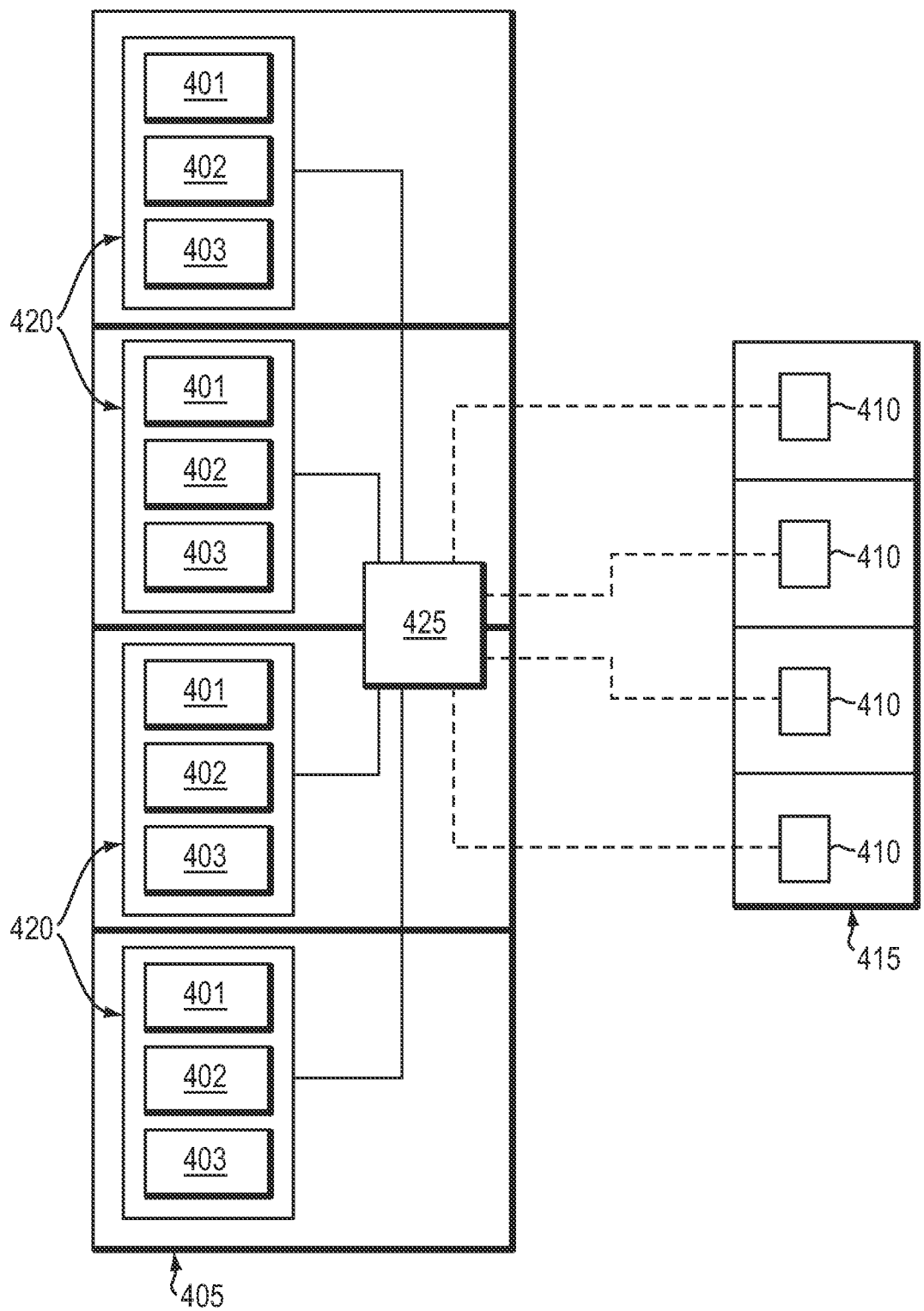
FIG. 4B illustrates an OCT imaging system incorporating multiple imaging engines that couple the assembly arms via the optical controller.

In various embodiments, as depicted in FIG. 4B, more than one imaging engine 420 may be deployed to handle the signals from the multiple sample arms 410. How many imaging engines are deployed for a given (and changing) number of sample arms depends on system configuration. If, as shown in FIG. 4B, each imaging engine 420 includes a light source 401 and interferometer 402 as well as processing hardware 403, then the optical controller 425 may activate an imaging engine which was previously off upon detection of a newly active sample arm, which is coupled to the activated imaging engine. Similarly, optical controller 425 may de-activate imaging engines upon detecting that the associated sample arms are no longer in use. In these implementations, the optical controller 425 acts as a simple switch matrix whose operation is governed by user demand. In more sophisticated implementations, the processing system 403 may be virtualized so that multiple software-based image-processing applications can be separately launched and run on a single computer, up to the limit of the computer's capacity to execute them. In such implementations, the light sources 401 and interferometers 402 may be collectively located in area 405 or instead in the various examination rooms 415. Optical controller 425 executes a queue management and/or load-balancing function that distributes demand from active sample arms to actively running image-processing applications, and launches new instances of the image-processing applications as these become necessary to accommodate demand. The system may include multiple computers (e.g., in a cloud configuration) so that once the multi-application limit of a particular computer is reached, a new computer (or new cloud-based computational capacity) is activated and image-processing applications launched thereon as necessary. Load-balancing software and virtualization and cloud architectures are very well known in the art and are straightforwardly adapted to the present context without undue experimentation.

In various embodiments the optical controller 425 and/or processing system 403 may be provided as either software, hardware, or some combination thereof. For example, the system may be implemented on one or more server-class computers, such as a PC having a CPU board containing one or more processors such as the Core Pentium or Celeron family of processors manufactured by Intel Corporation of Santa Clara, Calif. and POWER PC family of processors manufactured by Motorola Corporation of Schaumburg, Ill., and/or the ATHLON line of processors manufactured by Advanced Micro Devices, Inc., of Sunnyvale, Calif. The processor may also include a main memory unit for storing programs and/or data relating to the methods described above. The memory may include random access memory (RAM), read only memory (ROM), and/or FLASH memory residing on commonly available hardware such as one or more application specific integrated circuits (ASIC), field programmable gate arrays (FPGA), electrically erasable programmable read-only memories (EEPROM), programmable read-only memories (PROM), or programmable logic devices (PLD). In some embodiments, the programs may be provided using external RAM and/or ROM such as optical disks, magnetic disks, as well as other commonly used storage devices.

For embodiments in which the optical controller 425 and/or processing system 403 are provided as a software program, the program may be written in any one of a number of high level languages such as FORTRAN, PASCAL, JAVA, C, C++, C#, LISP, PERL, BASIC, PYTHON or any suitable programming language. Additionally, the software can be implemented in an assembly language and/or machine language directed to the microprocessor resident on a target device.

Figure 4C:
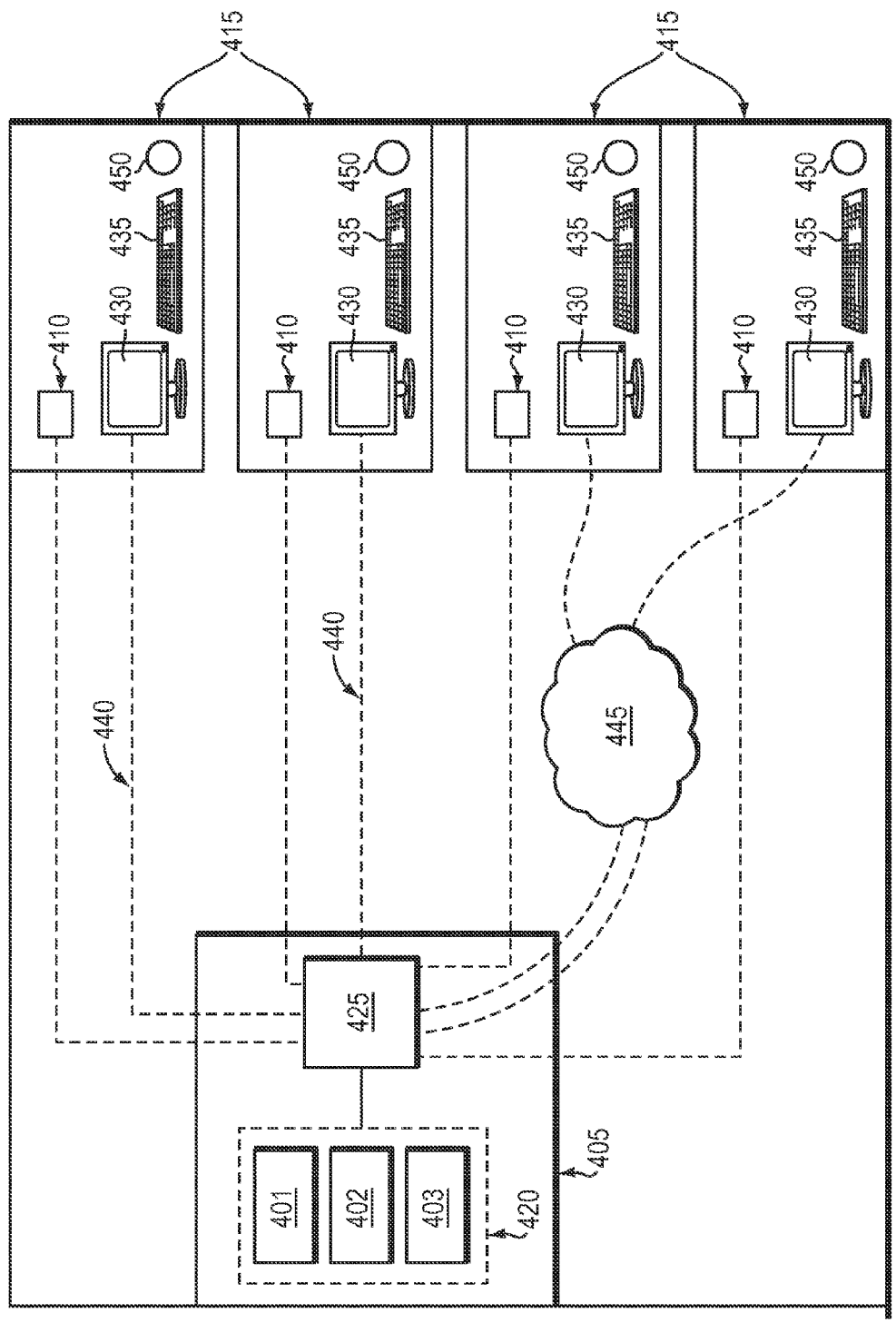
FIG. 4C illustrates an OCT imaging system with multiple sample arms installed in different rooms, separate from the imaging engine, with displays associated with the sample arm via direct point-to-point electrical connections and/or a local area network.

Referring to FIG. 4C, in some embodiments, a display 430 and control interfaces 435 may also be located in each examination room via point-to-point wiring 440 or a network interface 445. The display 430 and control interfaces 435 may also be included in the OCT system, thus allowing a user to view and manipulate the diagnostic images. The display 430 and control interfaces 435 may be provided as one integral unit or separate units and may also include one or more user input devices 450 such as a keyboard and/or mouse. The display can be passive (e.g., a "dumb" CRT or LCD screen) or in some cases interactive, facilitating direct user interaction with the images and models through touch-screens (using, for example, the physician's finger as an input device) and/or various other input devices such as a stylus, light pen, or pointer. The actual time required to capture an image in the OCT imaging system is minimal. Depending on the imaging application and the sample arm implementation, a particular sample arm may only need to be interfaced to (or communicate with) the imaging engine for several seconds or less in order to capture sufficient data for imaging or diagnostic purposes. Depending on the design of the interferometer, the total path length of light propagation in the reference arm is generally carefully matched (i.e., equal to within a coherence length) to that of the sample arms to ensure proper functionality of the interferometer. In one embodiment, the reference arm incorporates any of a variety of approaches to linear actuation (e.g., motor, servo, piezo drive, and/or other mechanical element) that is controlled by the imaging-engine hardware and software, which auto-adjusts the reference arm position to match path lengths between the sample and reference arms.

Figure 4D:
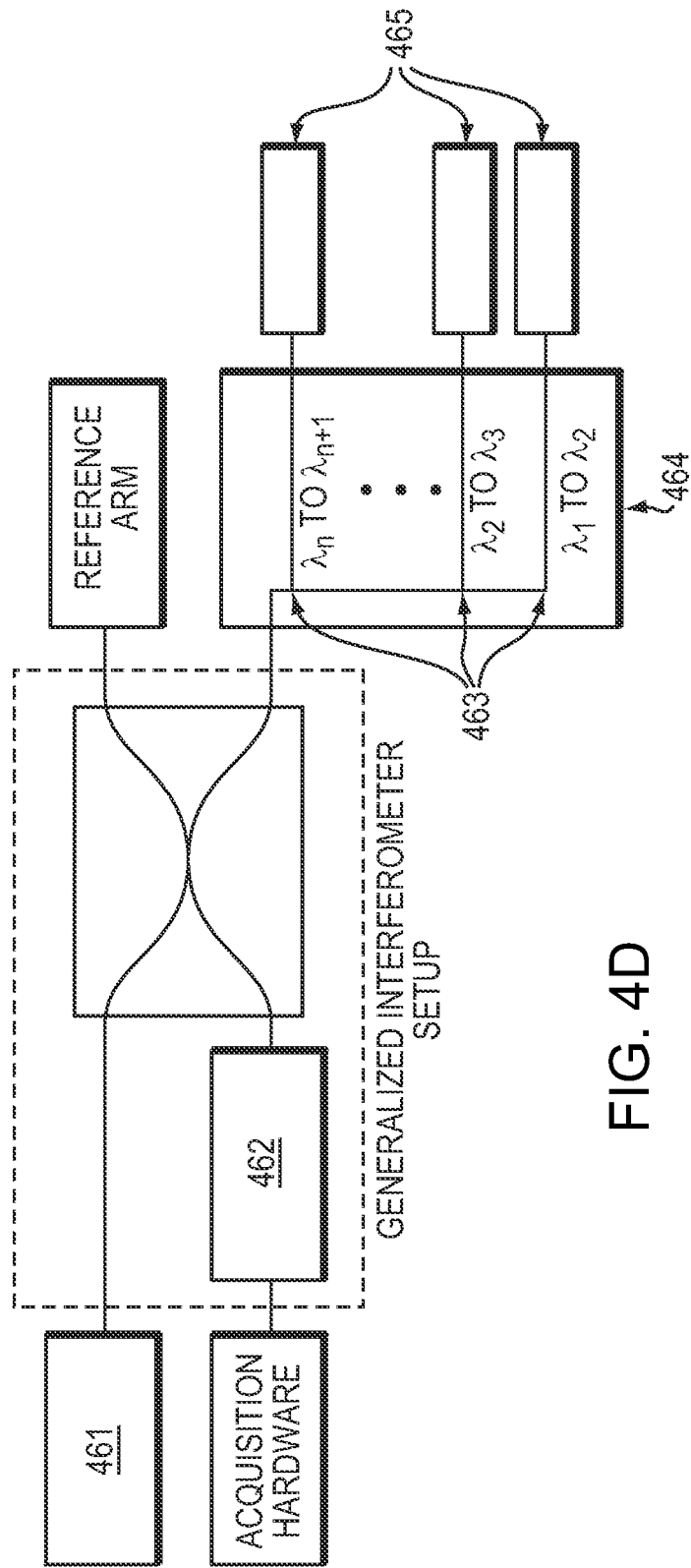
FIG. 4D illustrates a multiple-sample-arm configuration using a wavelength-division multiplexer as an optical controller.
Figure 4E:
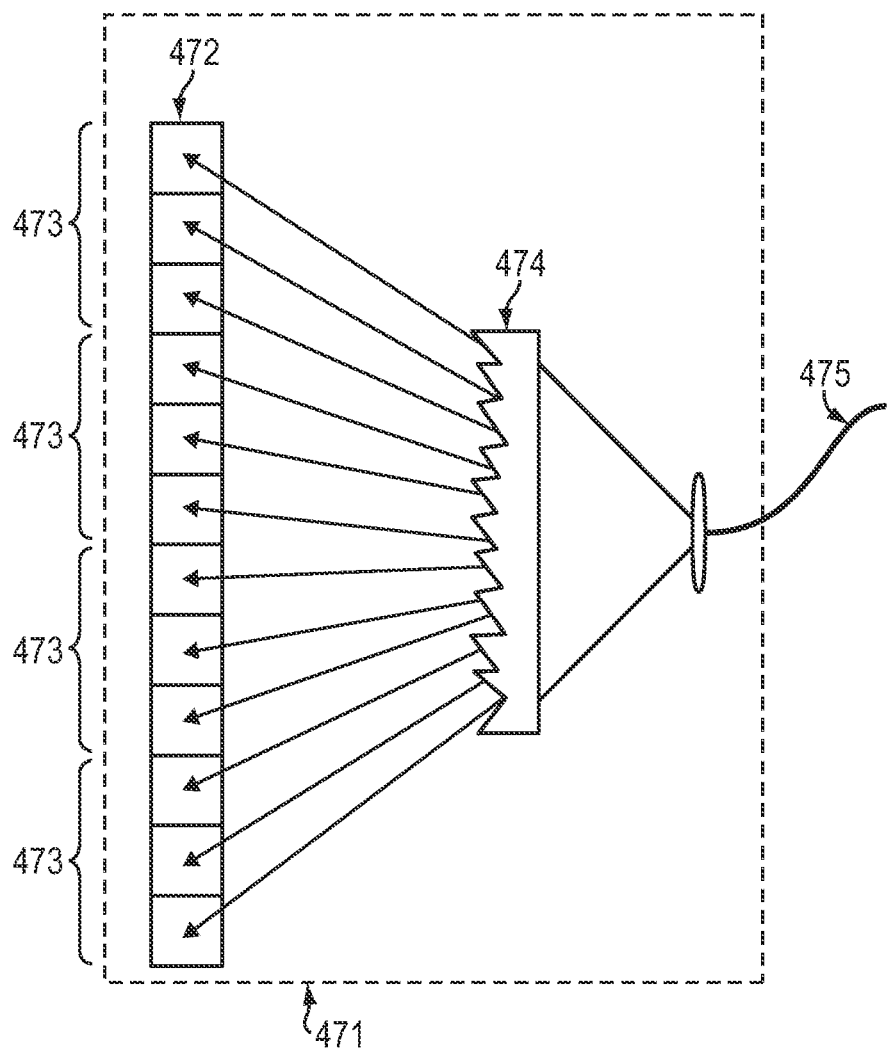
FIG. 4E depicts a spectrometer used to separate the wavelength components of a sample arm so that the separate wavelength components can be sampled by individual sensors in an array.
Figure 4F:
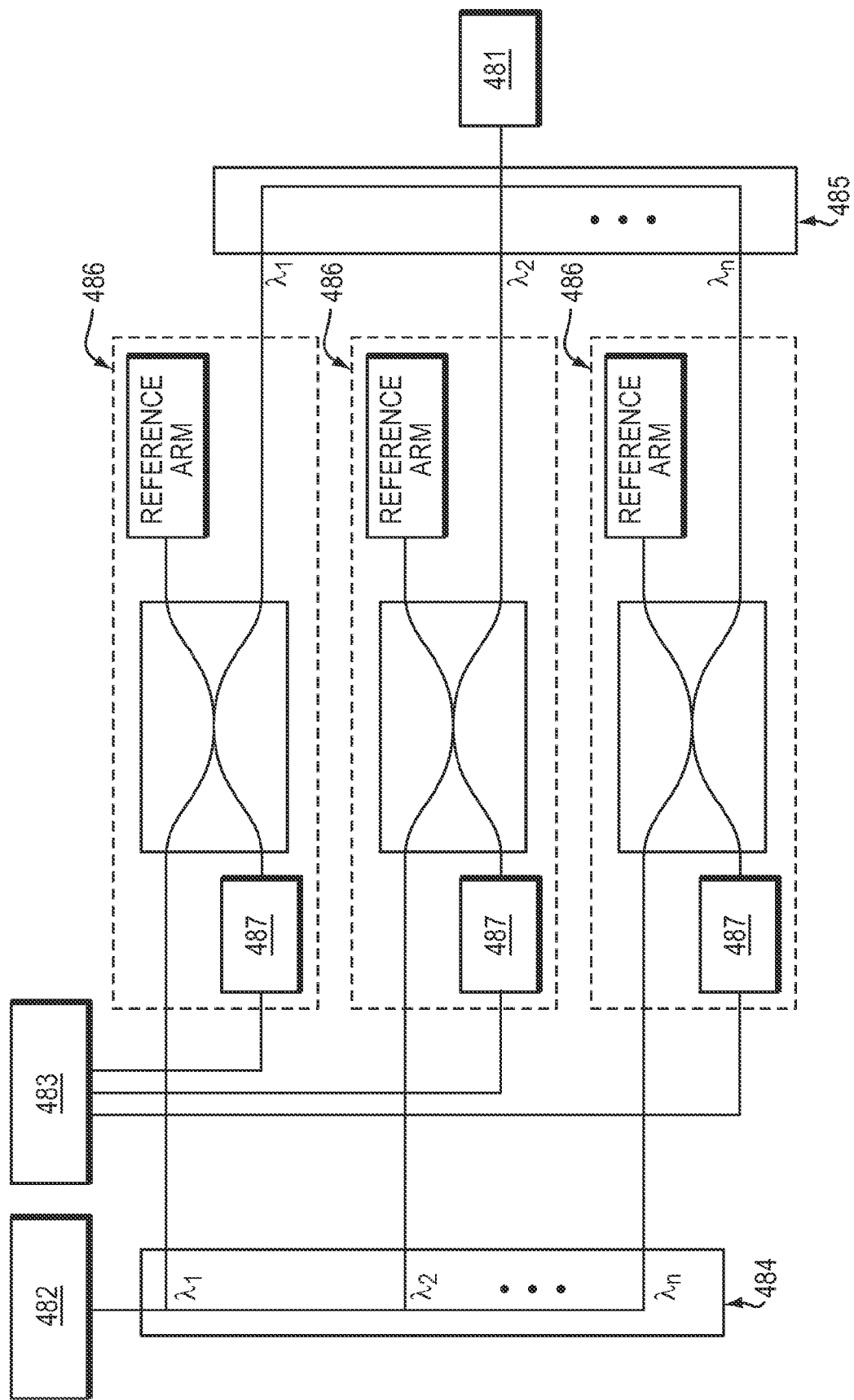
FIG. 4F depicts a single sample arm multiplexed into multiple wavelength OCT systems.

With reference to FIG. 4D, for example, using a spectrometer-based OCT interferometer configuration, including a broadband light source 461 (such as one or multiple super-luminescent diodes or a super-continuum laser with a bandwidth sufficient for the number of desired sample arms), a spectrometer 462, and properly chosen filters 463 in the WDM 464 (e.g., thin films or interference filters with sharp cutoffs), each sample arm 465 operates over a different range of wavelengths (e.g., 50-150 nm wide each). The spectrometer 462 isolates and samples the bandwidth of each discrete band within the wavelength range of each sample arm 465. FIG. 4E depicts a spectrometer 471 containing multiple sensors 472 in an array, with different sensors optimized for different wavelengths 473, and/or gratings 474 for separating the wavelength components for each sample arm 475. The cutoff filters that have roll-off or slope and a finite wavelength gap (e.g. 10-20 nm) between sample arms are desirable for avoiding overlap wavelength between the sample arms. The spectral bandwidth of the light source, the number of sample arms, and the spectral bandwidth of each sample arm dictate the resolution of the OCT imaging. The slope of the cutoff for each filter can be optimized for system performance.

In one embodiment, a single sample arm is wavelength-division multiplexed to multiple interferometers or components of an interferometer optimized for a particular optical spectrum. This embodiment enables a single instrument to perform OCT imaging at multiple wavelengths, for example, any combination of 830 nm, 1050 nm, 1310 nm, and 1550 nm wavelengths. There are both advantages and disadvantages for imaging at different wavelengths: for example, 830 nm light provides a better imaging resolution than longer wavelength light, but it does not penetrate certain biological tissues as deeply as longer wavelengths. On the other hand, 1310 nm light exhibits better penetration into tissue (e.g., the retina), providing a deeper imaging capability, but it is strongly absorbed by water and thus cannot be effectively used for imaging the retina externally through the cornea. FIG. 4D depicts a single sample arm 481, including an A-scan, B-scan, or C-scan capability connected to an OCT system that incorporates a broadband light source 482, data-acquisition, processing and display hardware 483, filters or wavelength-division multiplexer 484, a wavelength-division multiplexer 485, and multiple interferometers 486 and/or spectrometers 487, each optimized for a particular bandwidth. The broadband light source 482 may include multiple light sources with narrow bandwidths (e.g., 100 nm) at different wavelengths or a single broadband (e.g., 1000 nm) light source, such as a super-continuum laser.

Multiple fiber-based interferometers may be used to ensure single-mode operation at a broad range of wavelengths. For example, a 1310 nm light source utilizes a fiber with a core size of approximately 9 µm whereas an 830 nm light source uses a fiber with a core size approximately 4.5 µm for single mode operation. Likewise, different sensor technologies (e.g. Si vs InGaAs) are preferred for different wavelengths. The optical properties and the optical path length of the sample arm can be optimized to reduce the effects of modal and chromatic dispersion at the different wavelengths implemented, for example, by minimizing the optical path length of the sample arm.

In another embodiment, the WDM is eliminated altogether and the sample arms for each imaging wavelength are all arranged separately (i.e., not sharing a common optical path) within the OCT instrument.

Figure 5A:
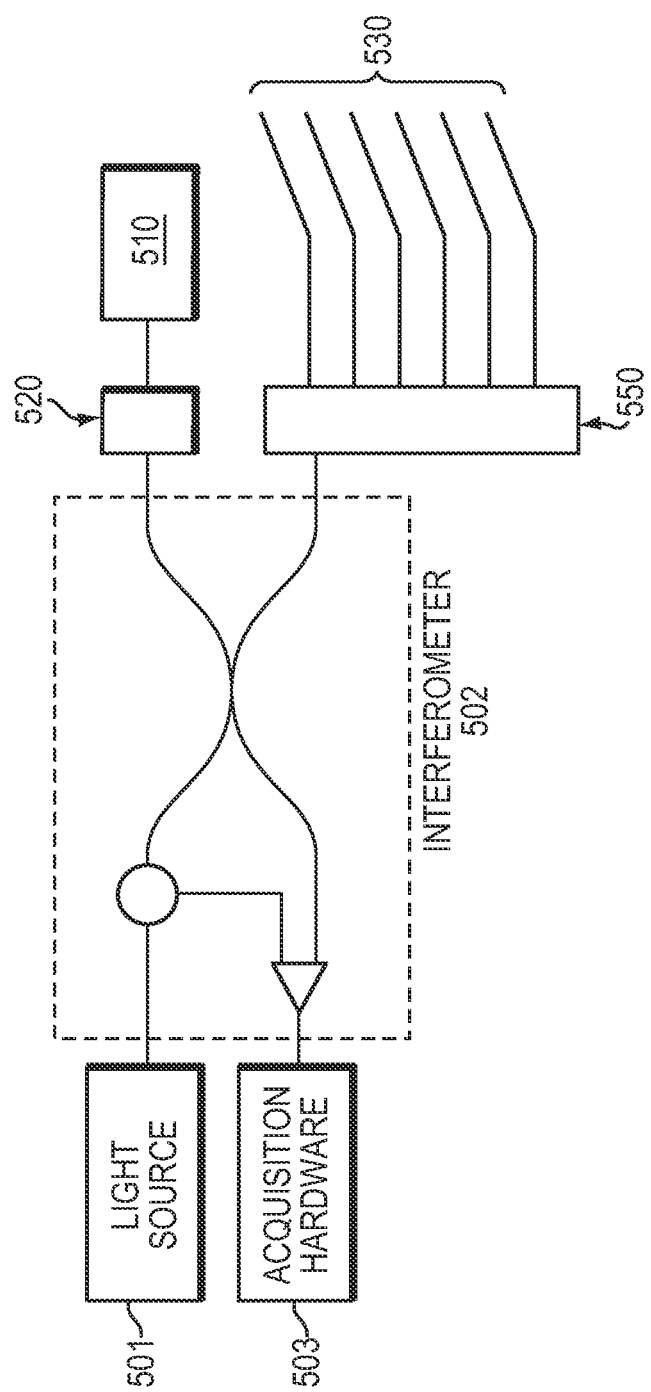
FIG. 5A depicts the reference arm in an OCT imaging system that incorporates a mechanical element for adjusting the reference arm position to match light path lengths between the sample arms and the reference arm. The multiple sample arms are connected to the imaging engine via an optical controller.
Figure 5B:
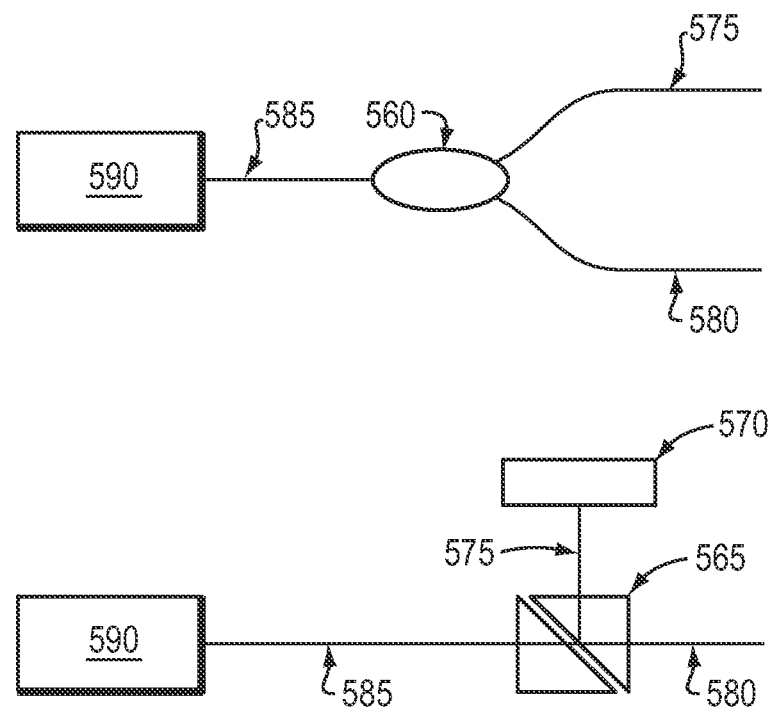
FIG. 5B schematically depicts an interferometer configuration in which the reference and sample arms share the same beam path.

FIG. 5A depicts an exemplary system in which a reference arm 510 incorporates a mechanical element 520 for adjusting a position thereof to select a light-path length between the reference arm and a light source 501 to match a light-path length between the light source 501 and the sample arms 530. A fiber-based optical delay line, composed of fiber-optic components (e.g., an optical cavity or two linearly chirped fiber Bragg gratings, fiber optic coupler, and circulator) can be used to replace the mechanical element 520 to manually or automatically match the path lengths as well. In an alternate embodiment, a common-path interferometer configuration, wherein the sample and reference arms share a common beam path with a reference plane defined by an optical surface near the front surface of a target, is used to eliminate the requirement of one or multiple reference arms and decrease sensitivity to path-length mismatches. Referring to FIG. 5B, the common-path configuration can be implemented by integrating the reference arm into the sample arm assembly. In some embodiments, the integration is implemented by incorporating, for example, an optical coupler 560 or a prism 565 and a reflector 570 (e.g., a mirror) to couple the reference arm 575 and sample arm 580 into a single fiber 585. Signals in the single fiber 858 are then delivered to the interferometer 590. The foregoing components form an integration system that can be very small (e.g., on the order of a few millimeters), where both reference arm and sample arm share an effectively common path, or very large if implemented in a large instrument (e.g., an ophthalmoscope), where the integrated reference arm is designed to properly match the length of the sample arm. The integration system can be handhold or mounted on an instrument.

A variety of sample-arm configurations (e.g., an OCT scanning ophthalmoscope, an OCT-enabled slit lamp, a minimally-invasive OCT probe, etc.) may be accommodated in each examination room by means of an optical-fiber connector that allows different sample arms to be readily connected to and disconnected from the remotely-located imaging engine.

OCT-Enabled Ophthalmic Instruments

A number of instruments are commonly used during ophthalmic examinations and surgical procedures to view both the anterior (e.g., the cornea) and posterior (e.g., the retina) segments of the eye, as well as external regions and structures related to and surrounding the eye (including but not limited to the eyelids, eyelashes, tear ducts, etc.). These instruments include but are not limited to the slit-lamp, the indirect ophthalmoscope, and the binocular microscope. Embodiments of the present invention incorporate an OCT imaging system with or into any of these instruments. Embodiments may provide a visual image of the target in the ophthalmic instrument simultaneously with a real-time OCT image of the target; the visual image and OCT image are generated in a time-synchronized and, in some cases, superimposed manner. Embodiments include imaging systems in which the OCT engine is remotely located, as well as imaging systems in which the OCT engine is located adjacent to the sample arm (e.g., in the same enclosure or in the same room).

Figure 6A:
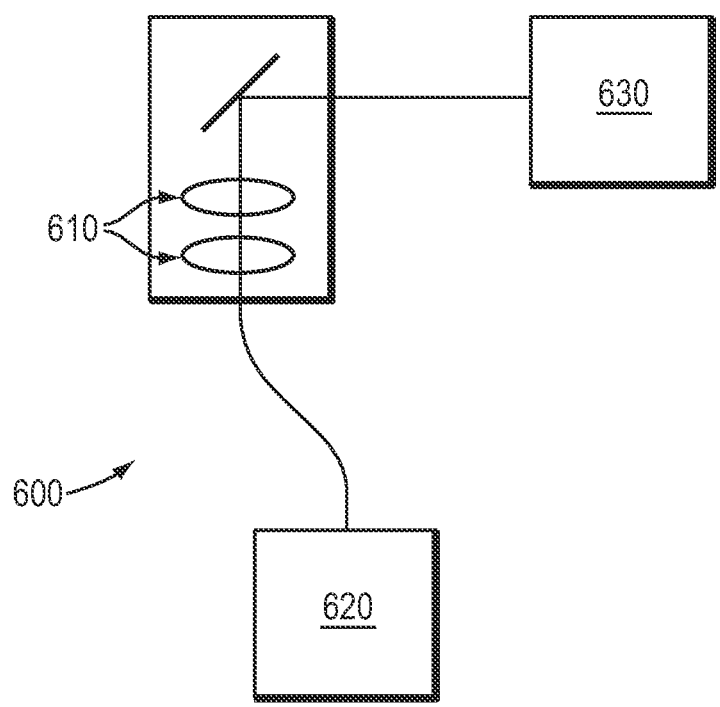
FIGS. 6A and 6B depict an OCT imaging system for providing A-scan and B-scan images of the target, respectively.
Figure 6B:
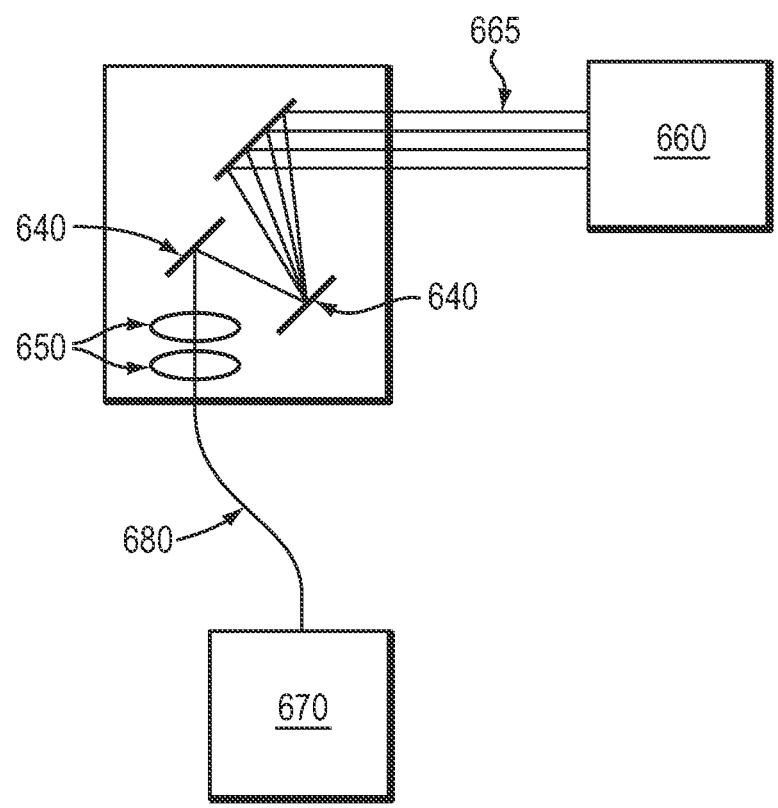

An A-scan provides one-dimensional axial depth scans of the tissue of interest, thus providing information on the identity, size, and depth of subsurface features. FIG. 6A depicts a system 600 having a lens system 610 (e.g., for collimation or focusing) integrated into the OCT system 620 and a target 630. This system 600 enables one-dimensional single OCT A-scans to be obtained at the central point of the target; it may also provide B-scan or C-scan imaging by tracking the manually moved system 600 using, e.g., a gyroscope, an accelerometer, or an optical tracking system, and subsequently combining the consecutive and spatially adjacent A-scans in software. A series of spatially adjacent A-scans (typically lying in a straight line) may be combined to form a B-scan, which provides a two-dimensional reconstructed image of the imaged area. In various embodiments, the ophthalmic instrument includes or is used in conjunction with an OCT sample arm assembly that includes a method for scanning (e.g., raster scanning) the OCT laser in one or two dimensions, producing an A-scan or B-scan, respectively. FIG. 6B shows how a scanning system 640 may be coupled to the lens system 650 to produce a two-dimensional, cross-sectional view of the target 660. Suitable scanning systems, include but are not limited to, a single-axis or double-axis scanning-mirror galvanometer, a MEMS scanning mirror, a piezoelectric scanner, an electro-optic crystal (e.g., KTN or lithium niobate) whose refractive index changes upon an applied electric field, or an optical phased array (e.g., LCD-based). Light traces 665 indicate the position of a single scanning laser beam at different times, instead of multiple concurrent light beams.

Figure 7A:
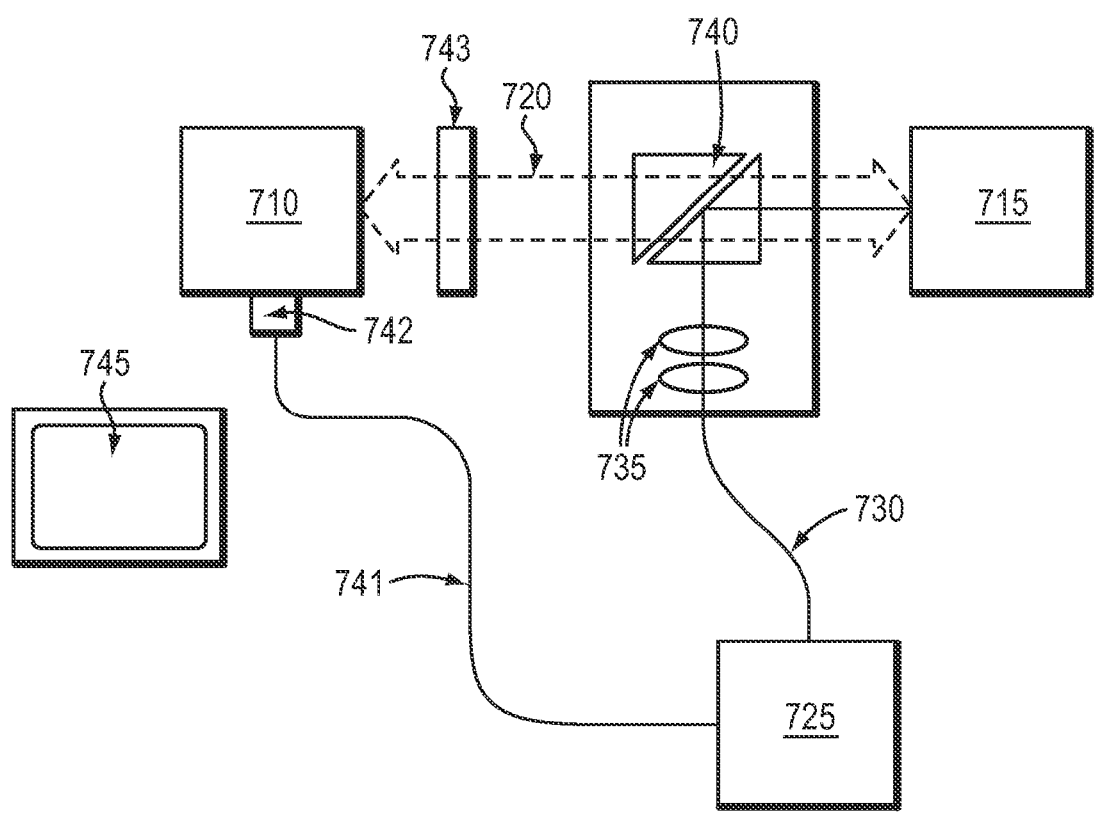
FIGS. 7A and 7B illustrate an OCT imaging system for A-scan and B-scan imaging, respectively, coupled to an optical instrument.
Figure 7B:
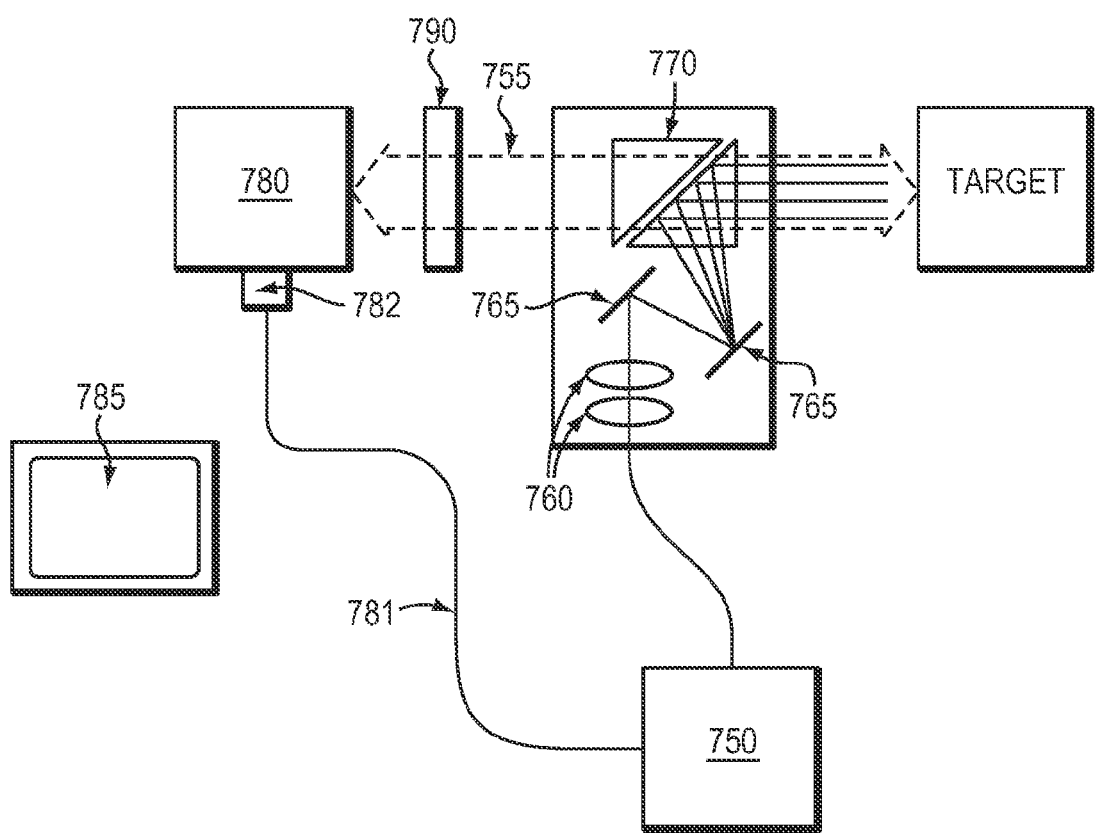

In one embodiment, an A-scan OCT imaging system is coupled to an ophthalmic instrument. Referring to FIG. 7A, light emitted from the optical instrument 710 upon a target 715 creates an optical path 720. An OCT system 725 including or used in conjunction with an optical fiber 730, a lens system 735 (e.g., for collimation or focusing), and an optical element 740 is coupled to the optical path 720. The optical element, for example, may be a prism coated with a thin film that reflects infrared wavelengths used for OCT but that transmits visible light used for illumination during the examination, depending on the prism configuration, or other suitable optical elements that may be used to couple the OCT light into the optical path of the examination instrument non-destructively, i.e., without degrading operation of the latter. The illustrated embodiment enables single OCT A-scans to be obtained at the central point of the area under examination by a surgeon. In additional A-scan embodiments, the fiber 741 is connected directly to the ophthalmic instrument 710 via use of, for example, the fiber connector 742 employed in a therapeutic laser-treatment system. An optical filter 743, located between the illumination source of the ophthalmic instrument 710 and the optical element 740, may be included to eliminate undesirable wavelengths created by the illumination source. For example, an infrared filter can be used to eliminate infrared wavelength that may interfere with the OCT signal (e.g., by saturating the sensor); a short-wavelength filter can be utilized to filter out shorter wavelengths (e.g., light in the 400 nm range) that may damage the retina. In another embodiment, a B-scan OCT imaging system is coupled to the ophthalmic instrument. With reference to FIG. 7B, the OCT system 750 is coupled to the light path 755 via a lens system 760, a scanning system 765, and an optical element 770. Utilizing the scanning system 765, this embodiment provides a two-dimensional reconstructed image of the imaged area, offering surgeons a visual reconstruction of subsurface features. In another embodiment, the B-scan OCT imaging system 750 is coupled to or integrated into the ophthalmic instrument 780 that delivers a therapeutic laser via a fiber 781 and a fiber connector 782 on the ophthalmic instrument 780. In another embodiment, an imaging system with C-scan capabilities is implemented by incorporating a scanning system capable of controlling the beam deflection in two dimensions.

Figure 8A:
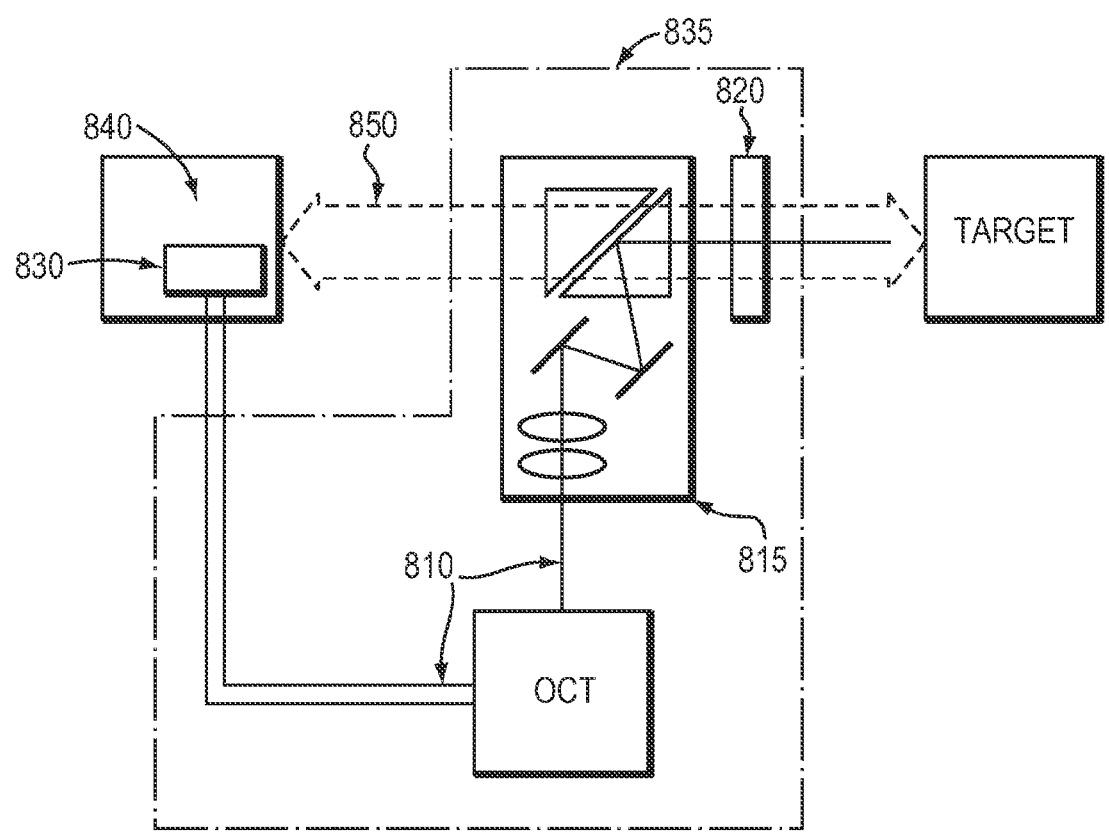
FIG. 8A depicts a combination, including the scanning system, the lens system, and the prism, attached on a swivel arm and an arm assembly joint attached to a mechanical frame of an optical instrument, thus enabling a user to easily move the OCT imaging system in and out of the optical path.

The A-scan and B-scan sample-arm assemblies may be held in the optical path by hand (e.g., by a surgeon or nurse), or they may be mounted in a fashion that enables automatic (e.g., actuated by the imaging system) or manual (e.g., positioned by the doctor) insertion or removal of the assembly from the optical path. One embodiment, as depicted in FIG. 8A, incorporates the combination 815, including the scanning system, the lens system, and the prism, on a swivel arm 820 or jointly attaches the arm assembly 810 to the mechanical frame 830 of the examination instrument 840, thus enabling the doctor to easily move the OCT imaging system 835 in and out of the optical path 850.

Figure 8B:
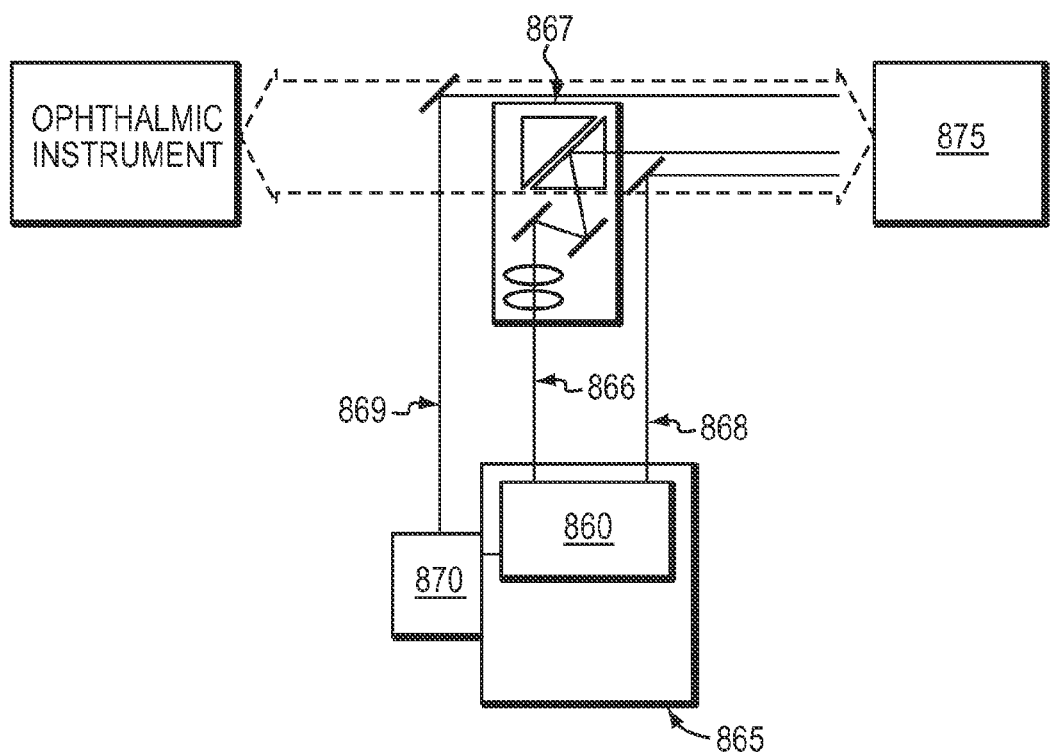
FIG. 8B depicts a therapeutic laser associated with the OCT imaging engine for providing simultaneous imaging and treatment of the target.

In one embodiment, an optical fiber used to carry the OCT laser light to the OCT imaging engine may also provide therapeutic laser capabilities (e.g., 532 nm photocoagulation). FIG. 8B illustrates how a therapeutic laser 860 may be integrated with the imaging engine 865; alternatively or in addition, a therapeutic laser 870 may be installed adjacent to the imaging engine 865. The therapeutic lasers 860 and 870 may share the same optical path 866 and scanning system 867 as the imaging engine 865 or may instead have their own optical paths 868 and 869, respectively, to the target. The scanning capabilities of the OCT sample arm may be used to direct the focal point of the treatment laser to the appropriate location on the target 875. This may significantly improve the precision of the treatment, eliminate image registration errors, and/or streamline the procedure by enabling the surgeon to examine the region of interest using multiple imaging modalities simultaneously (e.g., visual, topographic, or OCT) and to treat the relevant areas at the same time. Furthermore, the surgeon may verify the quality of the treatment burn in real time.

Figure 8C:
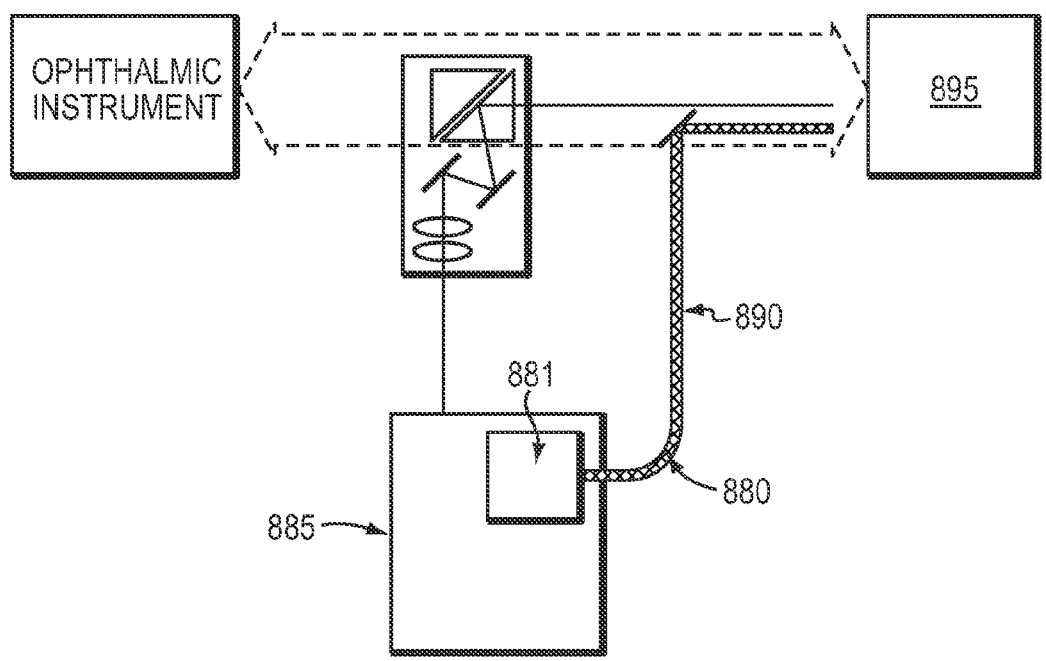
FIG. 8C depicts an optical element mounted onto the light source of the OCT imaging engine for providing illumination of the target.

In another embodiment, white light or broadband light over the visible spectrum that is sourced from the adjacent or remotely-located imaging engine may be incorporated into the combined instrument to provide illumination of the region under examination. FIG. 8C illustrates white light or broadband light 880 emitted from the light source 881 of the imaging engine 885 and propagating along a separate, larger diameter optical fiber 890 (e.g., multi-mode fiber), rather than the single-mode fiber, for providing sufficient intensity for white-light illumination on the target 895. Another option is the use of multi-clad or photonic crystal fiber having multiple waveguides that may be designed and optimized for the intended purpose (e.g., containing both single-mode for OCT and multi-mode for white light).

It should be noted that although the above descriptions relate to an OCT-enabled ophthalmic instrument, other imaging modalities that rely on similar optical configurations (particularly in the use of optical fiber and optical components similar to those described herein for illumination and/or light collection, and also modalities involving scanning mechanisms) may be used in accordance with the teachings hereof. For example, two-photon microscopy, two-photon excited fluorescence, scanning laser ophthalmoscopy (SLO), and/or confocal microscopy can all be used in the manner described herein, i.e., in lieu of or in conjunction with OCT capabilities.

OCT-Enabled Slit-Lamp

Figure 9:
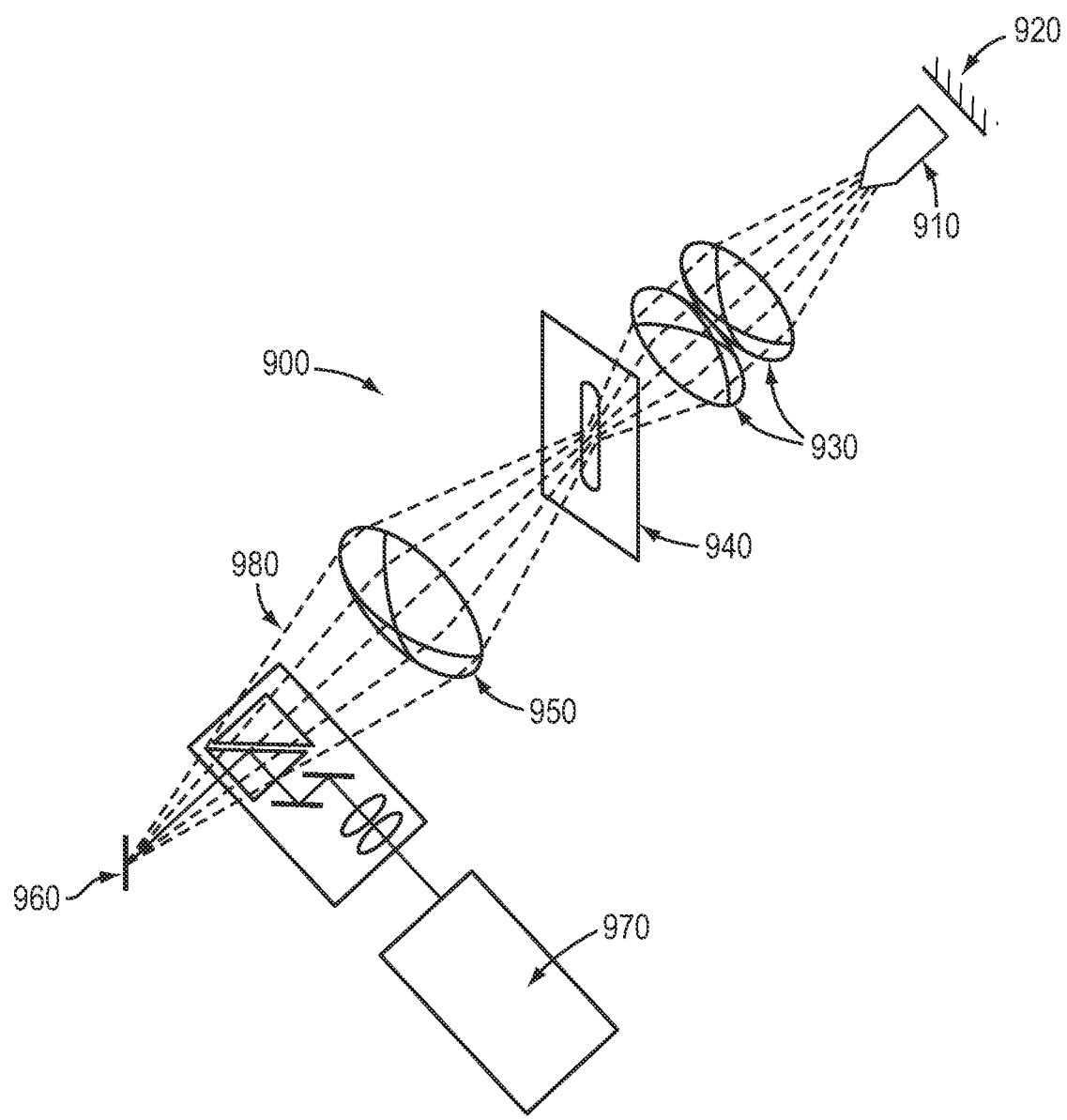
FIG. 9 illustrates the illumination system of a slit lamp.

Slit lamps are the ophthalmologist's most frequently used and most universally applicable examination instrument. Slit lamps are used in the examination of the anterior segment of the eye (e.g., crystalline lens) as well as the posterior segments (e.g. retina) with supplementary optics, such as contact lenses. The illumination system of slit lamps is intended to produce a uniformly bright, accurately focused slit of light whose dimensions can be adjusted. With reference to FIG. 9, the illumination system 900 of a representative slit lamp includes a light source 910 (e.g. halogen), a reflector 920 (e.g., a mirror) positioned behind the light source to maximize illumination, condensing lenses 930 (e.g. a pair of aspheric plano-convex lenses), a slit aperture 940, and a projector lens 950. The light source 910 is positioned at principle focus of the first condensing lens. The projector lens 950 projects the focused light at the slit 940 to a target 960. An observation system, which has a design analogous to a telescopic lens system, is then coupled to the illumination system 900 for magnifying and viewing the target.

Embodiments of the present invention incorporate an OCT imaging system 970 to couple non-destructively to the light path 980. The illustrated embodiment includes an OCT-enabled slit lamp designed to provide a doctor with both magnified visualization of the structure of interest as well as real-time OCT reconstructed images. A sample-arm assembly including a prism (e.g., with a thin-film coating that reflects OCT-wavelength light and transmits visible wavelengths) or other arrangement for combining the output of a single fiber and collimating lens with the light from the slit lamp may provide A-scan capability of a single point of interest, as depicted in FIG. 7A. Embodiments may also includes a scanning mechanism in the slit lamp that enables B-scan functionality, as shown in FIG. 7B.

In addition, variable-focus capabilities may be included by providing a means to adjust the spacing of lens components, such as the condensing lenses 930 and/or the projector lens 950, in the optical path and the distance to the eye to adjust the focal point. For example, variable focus may be used to alternate between OCT imaging of the anterior and posterior segments of the eye.

The sample arm assembly may be incorporated into the slit lamp frame, or it may be mounted externally for easy insertion into and removal from the optical path as shown in FIGS. 7A and 7B. In various embodiments, the reconstructed OCT image is displayed on a small monitor 745, 785 located adjacent to the slit-lamp for displaying a real-time OCT image of the target proximate a visualization of the target displayed on the slit-lamp. Although the OCT and slit-lamp images display different perspectives (e.g., topographical/surface vs. cross-section), in some embodiments the two images may be combined into a single composite image with enhanced visual features.

OCT-Enabled Indirect Ophthalmoscope

Figure 10A:
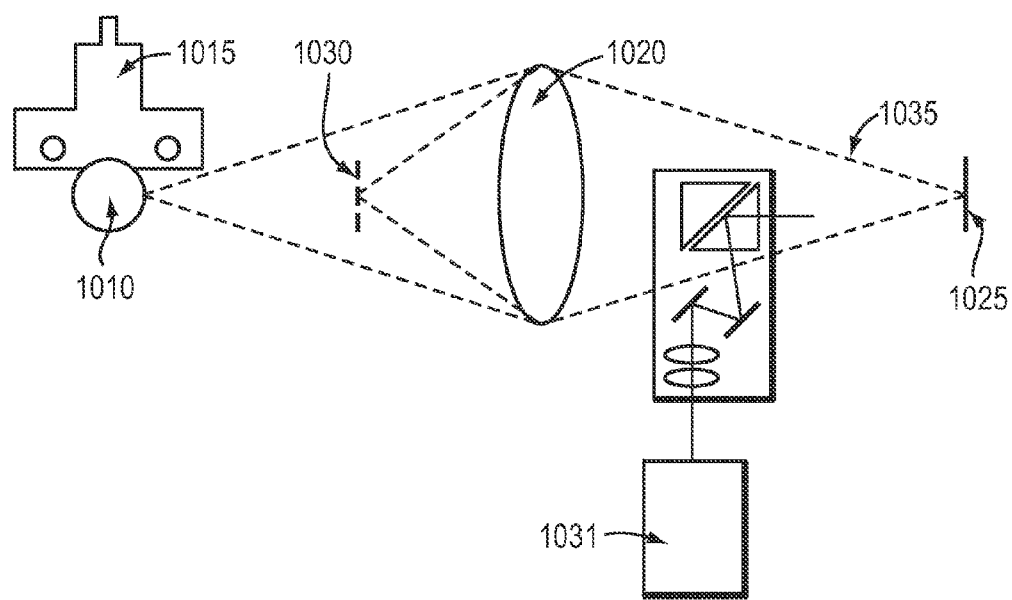
FIG. 10A illustrates the optics of an indirect ophthalmoscope.

An ophthalmoscope is an instrument for inspecting the interior of the eye; it allows a better view of the fundus of the eye, even if the lens is clouded by cataracts. An indirect ophthalmoscope can be either monocular or binocular; it provides a wide angle, bright, binocular view of the retina, while allowing the observer to maintain an arms-length distance from the patient. Referring to FIG. 10A, an indirect ophthalmoscope constitutes a light source 1010 (e.g., halogen) attached to a headband 1015, in addition to a small hand-held lens 1020. The hand-held condensing lens (e.g., aspheric convex lens) gathers light coming from the ophthalmoscope's light source 1010 to illuminate the retina 1025, and gathers it again for the benefit of the observer after it has left the subject eye. Light coming from a point on an emmetropic subject's retina leaves that eye as a bundle of parallel rays. The condensing lens focuses that bundle to a position 1030 closer to the observer, who therefore perceives an inverted image of the retina closer to his eye than the lens in the hand. In case the observer is presbyopic, the ophthalmoscope is fitted with reading glasses, so that focusing will not be necessary to see this image, which is about as far away as the observer's wrists.

Figure 10B:
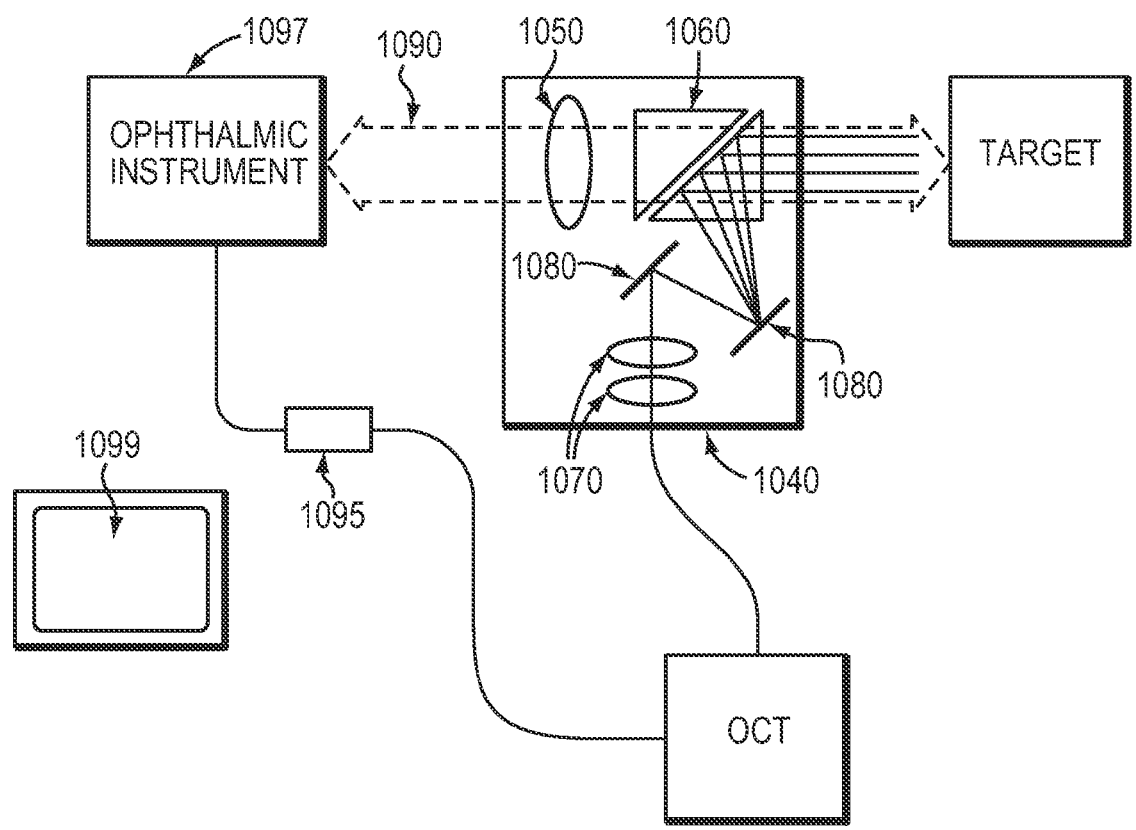
FIG. 10B illustrates an embodiment of a B-scan capable OCT-enabled indirect ophthalmoscope.

Embodiments of the present invention include an OCT system 1031 coupled to the optical path 1035 of the indirect ophthalmoscope system. Embodiments of the invention incorporate the sample arm in the doctor's ophthalmoscope headset, for example, by utilizing the same optical path as the illumination light source (e.g., halogen) and/or therapeutic laser from the ophthalmoscope. The therapeutic laser may be a high-power solid-state laser, such as a Nd:YAG 532 nm solid-state green laser, with a wide range of emission modes: single, repeat, continuous, and painting. The therapeutic laser may deliver multiple wavelengths to enhance the therapeutic effect. FIG. 10B depicts an exemplary B-scan-enabled indirect ophthalmoscope implementation. In typical usage, the doctor holds the assembly 1040 containing the condensing lens 1050, prism 1060, lens system 1070 and scanning system 1080 in the optical path 1090, adjusts the axial and lateral position of the assembly to bring the image into focus, and views and images the specific region of interest. The prism 1060 combines the transmitted OCT light with the visible light as it propagates into the eye and separates the reflected OCT signal from the visible light as it emanates from the eye. In alternative embodiments, the OCT sample arm assembly 1095 (including a prism, a lens system, and, in embodiments with B-scans, a scanning mechanism) is integrated into the indirect ophthalmoscope 1097 (e.g., doctor's headset) and utilizing the same optical path 1090 as the illumination light source and/or therapeutic laser; a standard condensing lens 1050 is used in normal fashion.

In addition, variable magnification may be implemented by using condensing lenses 1050 with different levels of magnification. In one embodiment, the reconstructed OCT image is displayed on a small monitor 1099 located within viewing distance of the doctor.

OCT-Enabled Binocular Microscope

Figure 11:
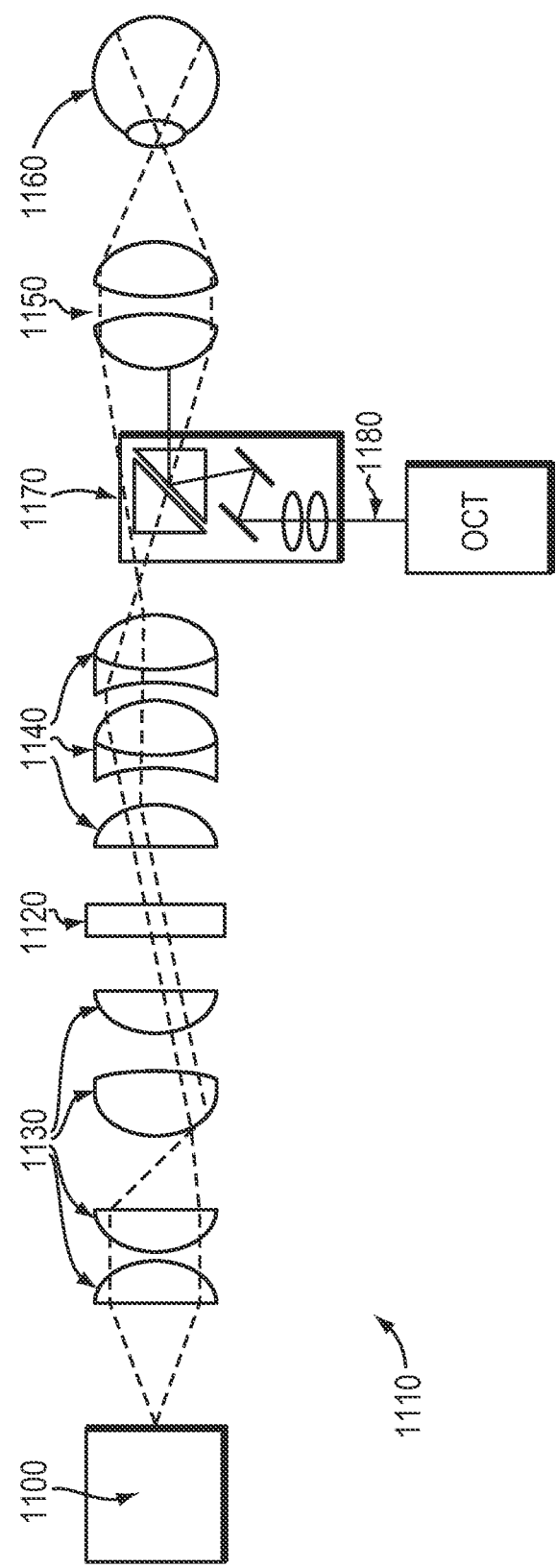
FIG. 11 depicts the optical path and components in a typical binocular microscope.

A binocular microscope is an instrument that magnifies the image of a target and provides a clear view of small and inaccessible parts of the target. With reference to FIG. 11, light from a light source 1100 (e.g., halogen) in a binocular microscope 1110 is collected and focused onto a target 1120 via a condenser system 1130. An objective 1140 is used to collect the light from the target 1120 and magnify the image of the target. The image is further magnified by eyepieces 1150 and projected onto human eyes 1160.

Embodiments of the present invention include an OCT-enabled binocular microscope that provides a surgeon with intra-operative OCT capabilities without impacting the use of the binocular microscope. In various embodiments, B-scan capabilities are enabled by an OCT sample-arm assembly 1180 (the arrangement of which has previously been described above) that is mounted on the microscope 1110 and which may be positioned in and out of the optical path 1170 of the microscope by the surgeon. Anterior segment scanning or retinal scanning may be selected by the insertion or removal of, for example, a binocular indirect ophthalmomicroscope (BIOM) lens, located in the optical path between the microscope and the patient's eye and mounted typically on a movable arm that can be swiveled into or out of the optical path, or a corneal-contact lens, placed in contact with the patient's eye, that changes the focal point of the optical system.

IOL Alignment

Figure 12:
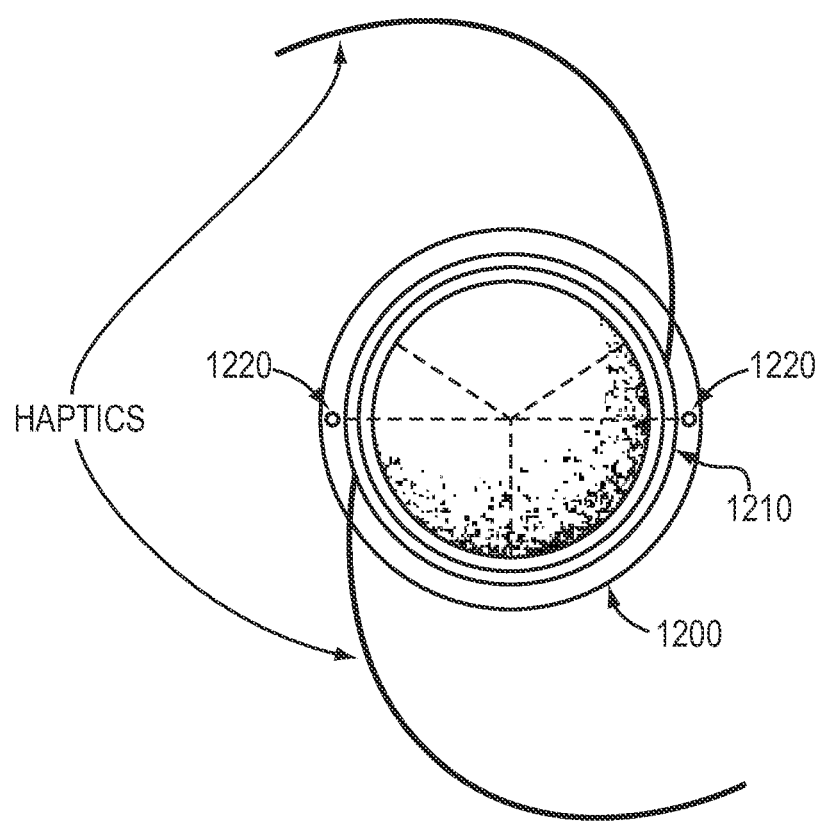
FIG. 12 illustrates an IOL showing the center point that may be identified using OCT to locate and measure concentric ridges or included fiducials.

In one particular embodiment utilizing a binocular microscope, an OCT-enabled visualization and imaging system enables the surgeon to properly align an intraocular lens during implantation. Embodiments of the present invention include a scanning mechanism coupled to an OCT imaging system (either locally or remotely located) that is placed in proximity to (but not necessarily in contact with) the eye. The scanning mechanism enables OCT imaging of both the anterior chamber and the posterior chamber (using a wavelength such as 830 nm) either by varying the position of the scanning mechanism (i.e., moving closer to or further from the eye) or varying the focal point of the laser through standard optical means. Furthermore, the imaging system includes software capabilities for identifying the precise center of the IOL by any or all of the following methods, as shown in FIG. 12:

1. Identifying the thickest region of the IOL 1200 (which typically corresponds to the central axis of a lens) based on the reflectance profile of the OCT signal to determine the maximum distance between detected reflections in the IOL;
2. Identifying the concentric ridges and grooves 1210 that encircle the IOL (similar to a Fresnel lens) that are present in some IOLs to provide focusing and variable length focal capabilities, and identifying the center of the IOL as the equidistant point centered within the innermost concentric ring; and/or
3. Using IOLs that contain fiducials 1220 or registration markers that may be identified by the OCT imaging system using conventional object-recognition algorithms (e.g., implemented in software along with OCT image reconstruction).

Any or all of the above methods may be used in conjunction with OCT imaging of the retina to identify the foveal pit (e.g., by switching between anterior and posterior focal points) to assist the surgeon in aligning the center of the IOL with the foveal pit (e.g., with overlaid images displayed on a monitor). The foveal pit may be identified either visually by the surgeon (e.g., by aligning crosshairs over the center of the foveal pit) or through computer vision and object-recognition algorithms programmed to identify the indentation at the foveal pit.

Additional embodiments simplify the system by replacing the scanning mechanism with a single fiber incorporating a focusing lens (e.g., a GRIN lens) for the purpose of capturing A-scans. A single A-scan may be used to identify the center of the lens and the foveal pit in combination with the previously described algorithms designed to identify the center of the IOL and the foveal pit. In such embodiments, the surgeon manually scans the optical fiber across the region of interest and is alerted to the proper alignment (e.g., via audio or visual cues).

Additional embodiments of the present invention include an A-scan- or B-scan-capable probe (e.g., including a scanning mechanism such as a side-scanning probe with a sub-millimeter probe tip diameter) for insertion into the anterior segment during the IOL implantation to provide similar imaging for the purpose of alignment.

While the foregoing descriptions focus primarily on ophthalmic applications, these technologies can be generally applied to any of a number of other medical fields that utilize imaging technologies, including orthopedics, dermatology, cardiology, gastroenterology, etc.

OCT and combination systems in accordance with embodiments of the present invention may incorporate any of a variety of features described in U.S. patent application Ser. Nos. 12/718,186, 12/718,188, 12/718,193, 12/718,266, and 12/718,272, the entire disclosures of which are incorporated by reference herein.

Image Capture and Display Technologies

The above-described implementations of different imaging systems typically provide for display of the reconstructed OCT image for viewing by a surgeon or clinician either in real-time or replayed at a later time. Embodiments of the invention include one or multiple displays (e.g., LCD or projection-based displays) for displaying OCT and other images. Additional embodiments incorporate one or multiple video cameras (e.g., digital cameras containing CMOS or CCD imaging sensors) that in conjunction with one or multiple displays provide substantially the same functionality and therefore replace a variety of imaging systems used by the surgeon, including but not limited to slit-lamps, indirect ophthalmoscopes, and binocular microscopes. The camera(s) are positioned to enable image capture of the region of interest and the display(s) are positioned to enable optimal viewing by the surgeon or clinician. For example, the camera(s) may be mounted on a fixture located above or in front of the patient or the camera(s) may be mounted in a headset worn by the surgeon or clinician.

Various embodiments display camera-captured images (e.g., in lieu of slit-lamp, binocular microscope, or ophthalmoscope usage), OCT captured data (e.g., A-scans, B-scans, and C-scans), or both. The OCT data may be displayed on the screen adjacent to or overlaid on the visible image(s) captured by the camera(s). The displayed image may be user-selectable between different image sources (e.g., OCT console and one or multiple cameras). The described imaging system may incorporate one or more of low-light, three-dimensional display, and high-resolution capabilities.

Low Light

In one embodiment, the imaging system incorporates low-light capabilities that enable the surgeon to visualize the structures of interest in a low-light setting or even in the absence of light (which is conducive to pupil dilation in the patient without using topical drugs). For example, low-lux cameras that exhibit high sensitivity to low light levels may be employed. Ambient light levels present from external sources (e.g., light leakage through window blinds, LCD backlight emissions, or light leakage through door cracks) may be sufficient for low-lux imaging. Alternately, the examination or operating room may be illuminated by a dim source of illumination in the visible spectrum to provide sufficient light for the desired low-light imaging capabilities. In another embodiment, the cameras are infrared-capable (e.g., the cameras are CMOS or CCD which is sensitive to infrared light and the cameras possess no infrared filters). An infrared illumination source is placed in the room to illuminate the structure of interest. This is advantageous because the patient's eye is not sensitive to infrared light and therefore the eye under examination can be brightly illuminated while fully dilated in the dark setting with no need for topical dilation drugs. An additional advantage is that the infrared OCT laser beam and the path it traverses (e.g., on the retina) is visible to the surgeon on the display, thus eliminating the need for a separate visible spectrum alignment beam.

3D Imaging

Current display technologies used in medical imaging and diagnostics display 3D structures in a 2D representation, resulting in a lack of depth information. Much of the detail gathered from a 3D imaging modality is lost in a 2D representation. There is a clear benefit for surgeons to be able to visualize imaged structures in 3D space. Embodiments of the present invention therefore can include multiple cameras positioned and aligned to capture 3D real-time video. The cameras can be mounted, for example, in the surgeon's headset or in a fixture positioned above or adjacent to the upright or supine patient. Implementations also include a display to provide 3D image reconstructions to the surgeon. In one embodiment, the surgeon wears a headset that contains two separate displays, one for each eye, each of which displays the image captured from a separate camera to provide a 3D image to the viewer.

In a second embodiment, the 3D image is created using conventional stereoscopic technology, which utilizes a pair of glasses or a headset (e.g., similar to a binocular indirect ophthalmoscope headset) that surgeons wear. In one embodiment, the stereoscopic effect is achieved through the use of glasses with different polarizing filters for each lens. The image presented to the display is a superposition of the two camera images through different polarization filters, each matched to one of the lenses in the glasses. In another embodiment, the glasses incorporate shutter technology (typically a LCD), wherein each lens can be independently and rapidly switched from visible to opaque. The glasses are synchronized to the refresh rate of the display; the display alternates images intended for one or the other eye and the synchronized shutters block the other eye.

Figure 13A:
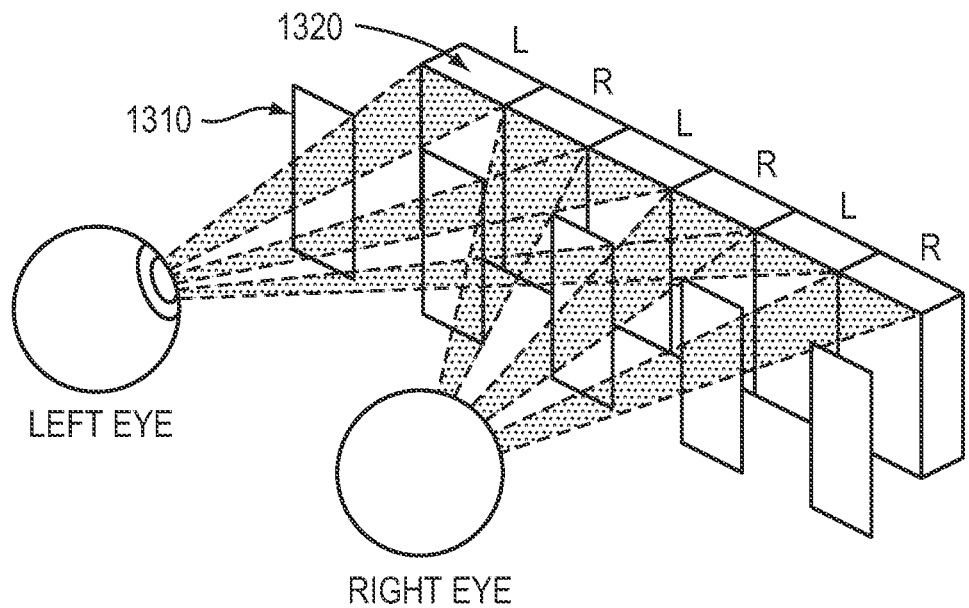
FIG. 13A depicts the working principle of three-dimensional displays.
Figure 13A:
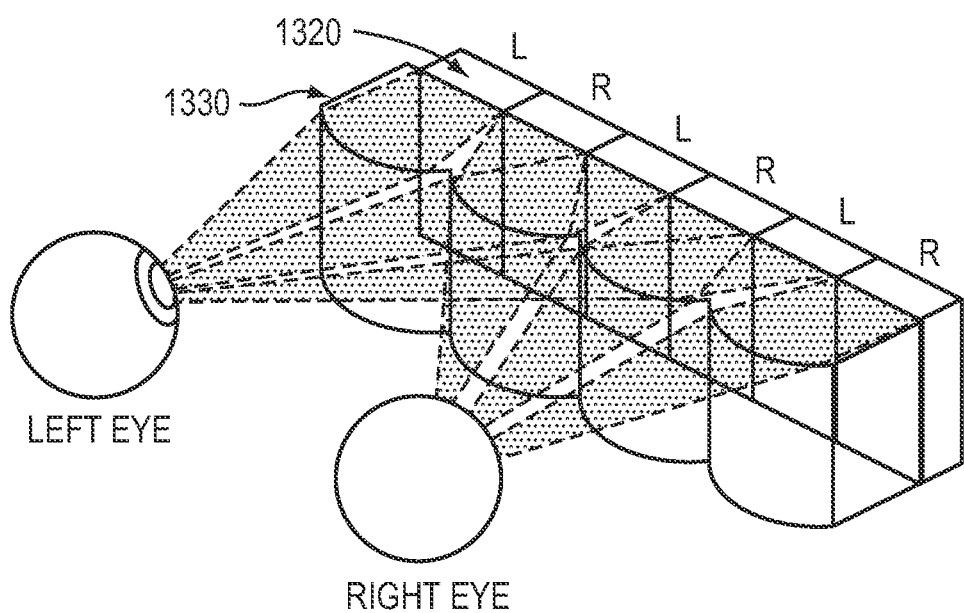
Figure 13B:
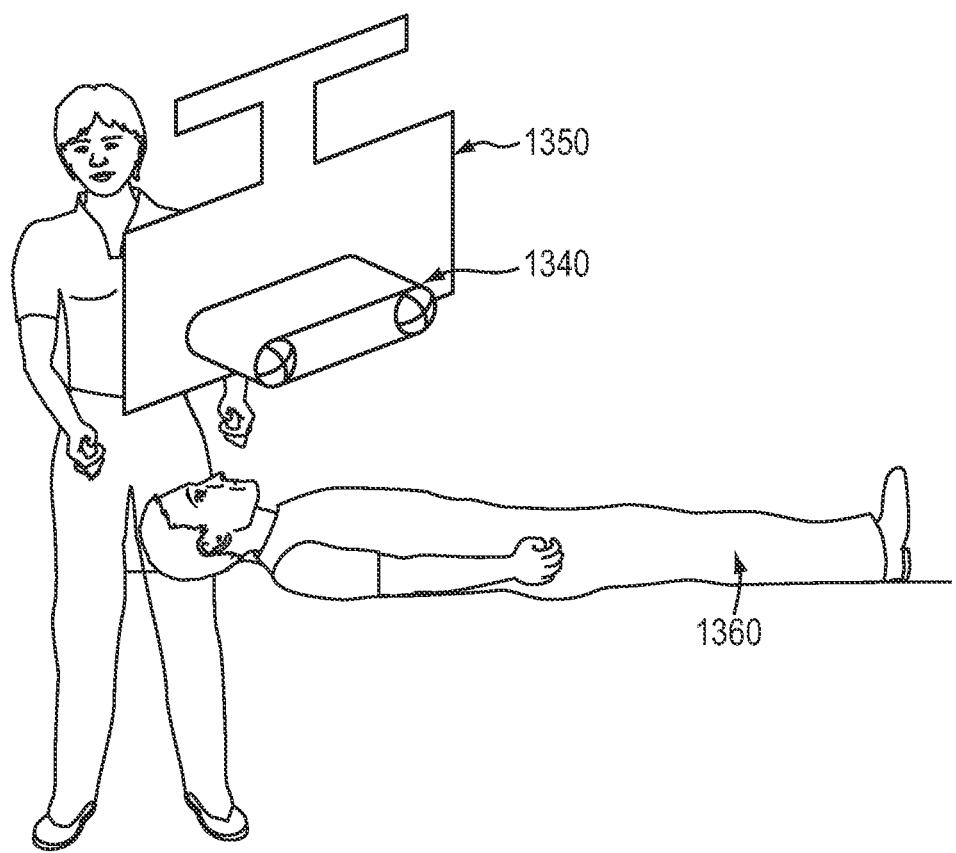
FIG. 13B illustrates dual cameras and a single display mounted above a supine patient.

In a third 3D display configuration, the 3D image is created via an autostereoscopic approach, which has the advantage of not requiring the viewer to wear a specialized pair of glasses. In one type of autostereoscopic display, a lenticular lens covers the display. Alternating pixel columns in the display are intended for the left eye and right eye; the shape of the lenticular lens ensures the light from each column of pixels refracts towards the proper eye. Referring to FIG. 13A, an alternate and potentially more cost-effective approach is to incorporate parallax barrier masks 1310 over the display 1320; this achieves a similar effect as the lenticular lens 1330. FIG. 13B illustrates an embodiment with dual cameras 1340 and an LCD display 1350 mounted above a supine patient 1360, appropriate for both use as a binocular indirect ophthalmoscope (in conjunction with a condenser lens) as well as a binocular microscope. A handheld sample arm assembly, as previously described, can be held in the optical path to enable OCT imaging (or, for example, two-photon fluorescence imaging). The display(s) and/or camera(s) may also be integrated into a headset.

The arrangement of multiple cameras can also provide benefits over single-camera optical-tracking systems that track the position and orientation of an instrument held by the surgeon; for example, a multiple-camera arrangement can be used to facilitate image reconstruction (for example, to stitch multiple A-scans together into a B-scan image). This is accomplished in one embodiment via using fiducial markers or indicators (easily recognized by the cameras, for example, as distinct colors, shapes, or infrared LEDs). Multiple cameras provide multiple angles at which to identify these fiducial markers and eliminate ambiguities in certain positions, thereby increasing the overall accuracy of the tracking system and reducing the computational requirements in some cases.

High Resolution

The use of high-resolution and high-definition display technologies offer benefits to surgeons, particularly ophthalmologists and other surgeons who image, diagnose, and treat biological structures that are invisible to the unaided eye. Embodiments of the systems described herein, including normal, low-light, and 3D imaging and for both visible and infrared light imaging, incorporate high-definition and high-resolution camera and display systems to provide increased clarity and resolving ability when visualizing small structures.

OCT-Enabled Electrodes

Current and emerging neural prostheses and therapies based on nerve stimulation and recording may involve electrodes chronically interfaced to the central and peripheral nervous systems. Electrical stimulation initiates a functional response by depolarizing the membranes of excitable cells. Depolarization is achieved by a current flow between two or more electrodes, at least one of which is in close proximity to the target tissue. In most neural applications, electrical stimulation is applied as a series of biphasic (i.e., cathodal and anodal) current pulses. The activity of neurons is recorded as an extracellular potential, or action potential, when the recorded signal identifies the firing of a single neuron (single-unit). Action potentials are recorded with electrodes implanted in close proximity to the target neurons. In general, the objective with single-unit neural recording is to measure action potentials with a useful signal-to-noise ratio, ~5:1 or greater, and to do this chronically.

Neurobiological research has used single-wire or glass micropipette electrodes to stimulate and/or record individual neuron waveforms in acute experiments. However, the need to access populations of neurons and the desire of researchers to monitor neural networks over time has led to development of arrays of wires, silicon shafts and other, more complex micro-machined silicon recording systems capable of high-density sampling. The efficacy of multiple electrodes used to stimulate or record neural activity in the brain, spine, and other regions of the body is typically heavily dependent upon accurate positioning of the electrodes. Additionally, the act of surgically placing the electrodes may introduce significant risk, especially if the electrodes are to be placed in a sensitive region such as the brain or spine. Many studies have attributed biologically induced electrode failure to the initial trauma of implantation, leading to a variety of strategies to minimize this early trauma in the hope of limiting the subsequent complications. Approaches include optimizing the speed of electrode insertion, the method of insertion, and the depth of insertion. Incorporating an OCT imaging system with electrodes may provide more accurate and detailed information about the accuracy and depth of insertion upon including the electrode in the tissue, thereby enhancing operational efficacy and decreasing risk to the patient.

Figure 14A:
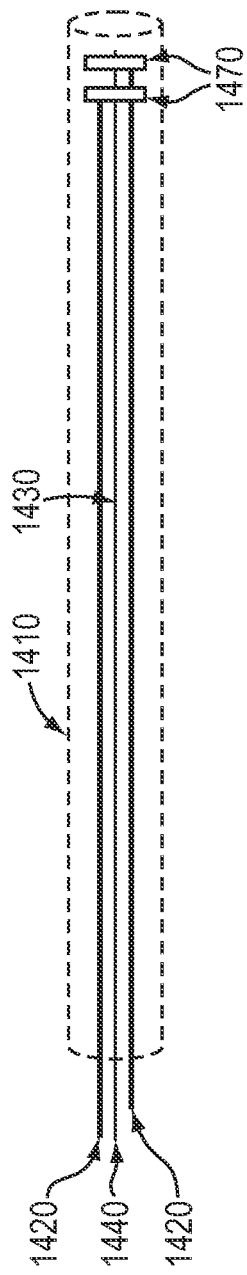
FIG. 14A depicts an OCT-enabled electrode.
Figure 14B:
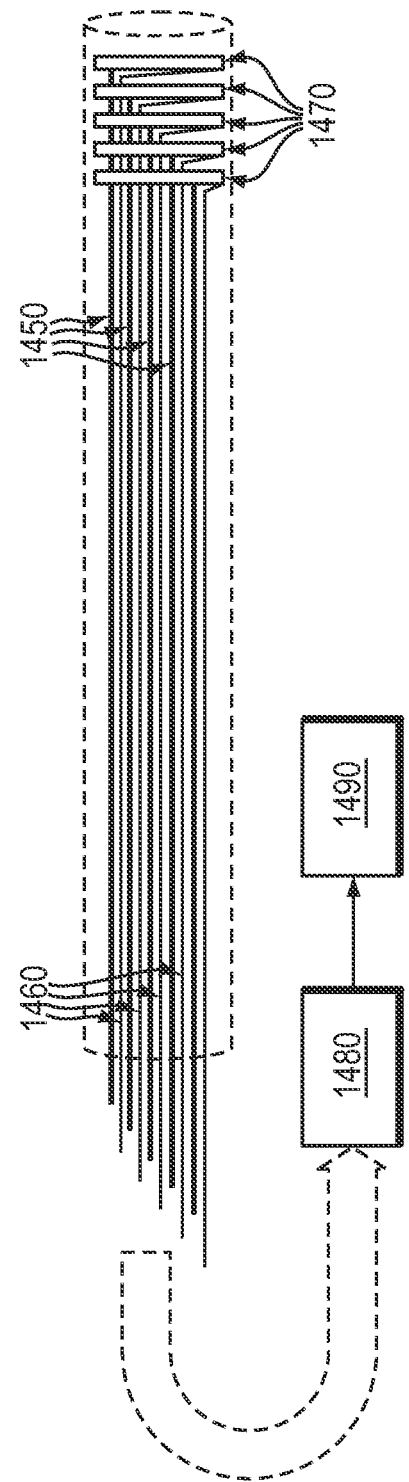
FIG. 14B depicts an OCT-enabled electrode array incorporating an optical controller to multiplex signals from the optical fibers.

Embodiments of the present invention incorporate an OCT imaging system into a neural stimulation- and/or neural activity-recording electrode or electrode array. FIG. 14A illustrates an electrode array containing an electrode carrier 1410, including two electrode leadwires 1420 and a single electrode channel 1430 with a single fiber 1440, associated with the electrode leadwires; the array is capable of A-scan OCT as described below. FIG. 14B shows multiple electrode channels 1450 with multiple A-scan-capable fibers 1460 (constituting a multiple-sample-arm configuration, as described above). Each individual optical fiber, which serves as an individual sample arm, has an end face capable of providing A-scan data of the region directly in front of the tip of the fiber. Each fiber is positioned in close proximity to a particular electrode contact 1470, such that the A-scan data captured by the optical fiber provides information regarding the tissue directly adjacent to the associated electrode contact 1470. The multiple electrode contacts 1470 are located at different positions along the distal end of the electrode carrier 1310; the electrode carrier thus captures optical information from the tissues adjacent to the contacts along the distal end of the carrier. A variety of configurations are possible depending on the application. In this particular example, the electrodes are made from a biocompatible electrically-conductive material such as platinum, while the flexible surrounding structure is made from parylene or another biocompatible polymer. In one embodiment, an optical controller 1480 (e.g., a wavelength-division multiplexer, a time-division multiplexer, or an optical switch) is incorporated to multiplex optical signals from some or all of the optical fibers to enable their convenient operation by and optical linkage to a centralized imaging engine 1490.

Figure 15:
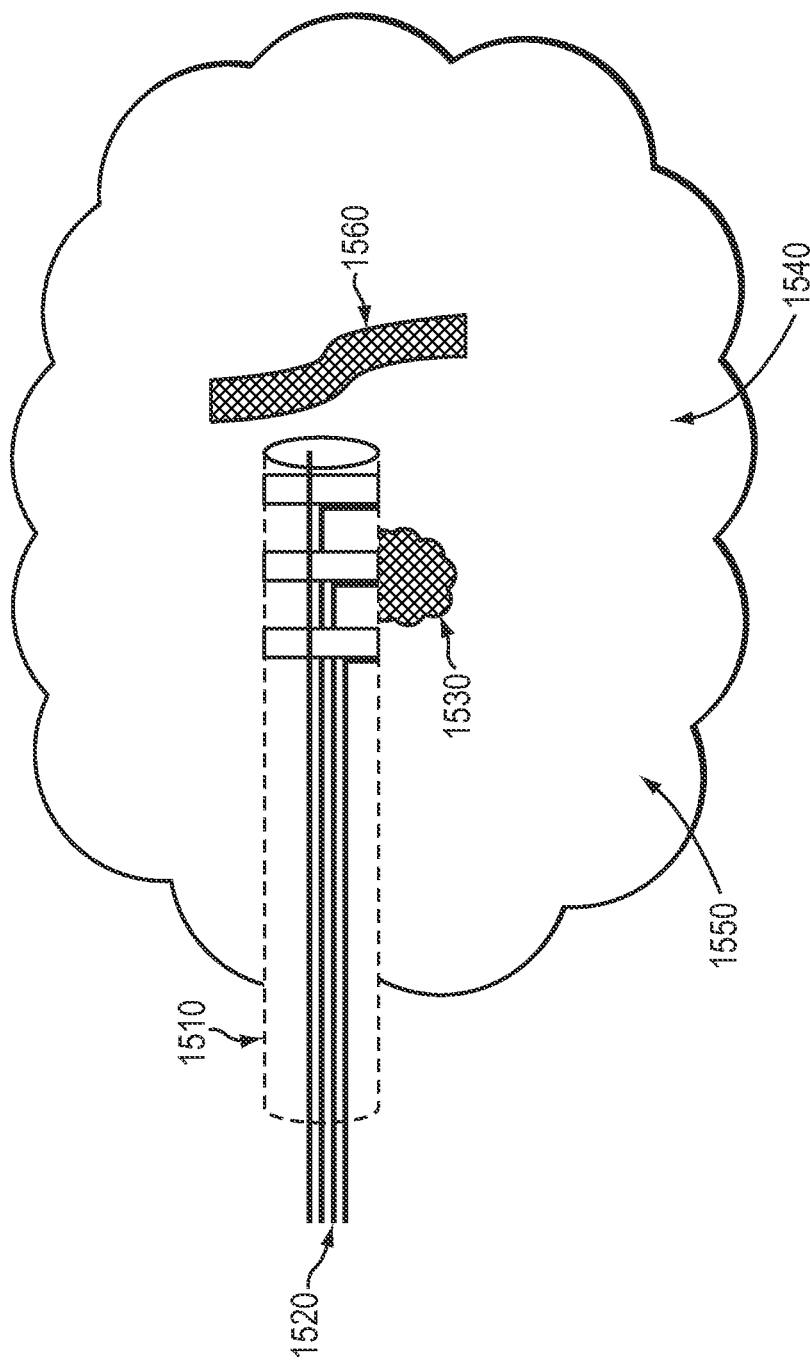
FIG. 15 illustrates one particular use of an OCT-enabled electrode array in brain tissue.

In some embodiments of the invention, as depicted in FIG. 15, the OCT-enabled electrode carrier 1510 including OCT fibers 1520 is used to differentiate between gray matter 1530, which is adjacent to the electrode carrier at the electrical contacts, and the surrounding tissue, e.g., white matter 1540, to optimally position electrodes in the brain tissue 1550. In another embodiment, the captured and processed A-scan data is used to identify the presence of specific structures forward of the electrodes. For example, the A-scan data may be used during the placement of electrodes to identify the presence of blood vessels 1560 before they are disturbed by the tunneling and positioning of the electrode. Furthermore, the optical fiber(s) may be used to propagate other wavelengths of laser light, e.g., for ablation purposes or to optically stimulate neuronal tissue.

The terms and expressions employed herein are used as terms and expressions of description and not of limitation, and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive.

What is claimed is:

1. A multiplexed OCT imaging system comprising:
a plurality of sample arms;
a plurality of reference arms, each at least partially sharing a common beam path with one of the sample arms with respect to a target;
at least one imaging engine; and
an optical controller,
wherein the sample arms are optically coupled to the at least one imaging engine via the optical controller, at least some of the sample arms being simultaneously operative to generate interference patterns (i) resulting from optical path-length or phase differences between the sample arms and corresponding ones of the reference arms and (ii) encoding spatial dimensions and locations of structures with respect to targets adjacent to the respective sample arms, the optical controller multiplexing optical signals separately representing the interference patterns simultaneously generated by the simultaneously operative sample arms.

2. The imaging system of claim 1, wherein the plurality of sample arms comprise optical fibers for transmitting light between the at least one imaging engine and the targets adjacent to the respective sample arms.

3. The imaging system of claim 2, wherein the optical fibers are single-mode optical fibers.

4. The imaging system of claim 1, further comprising display hardware associated with each sample arm for displaying images of the target.

5. The imaging system of claim 4, wherein the display hardware connects to the at least one imaging engine directly or via a local area network.

6. The imaging system of claim 1, further comprising a mechanical element for adjusting a relative position between the reference arm and the sample arm.

7. The imaging system of claim 1, further comprising an optical component for auto-matching the optical path-lengths between the reference arm and the sample arm.

8. The imaging system of claim 1, wherein the optical controller is a wavelength-division multiplexer.

9. The imaging system of claim 8, wherein the wavelength-division multiplexer comprises interference or thin film filters for avoiding overlapping wavelengths between each sample arm.

10. The imaging system of claim 1, wherein the optical controller is a time-division multiplexer or an optical switch.

11. A multiplexed OCT imaging system, comprising:
a plurality of sample arms;
a plurality of reference arms, each at least partially sharing a common beam path with one of the sample arms with respect to a target;
at least one imaging engine; and
an optical controller,
wherein the sample arms are optically coupled to the at least one imaging engine via the optical controller, the optical controller multiplexing optical signals from the sample arms to permit at least some of the sample arms to operate simultaneously and activating a new imaging engine upon detecting a new sample arm coupled to the newly activated imaging engine.

12. The imaging system of claim 11, wherein the activation occurs upon a detection of a demand issued by a user.

13. The imaging system of claim 11, wherein the optical controller is a switch matrix balancing loads among activated imaging engines to minimize the number of image-engine activations.

14. The imaging system of claim 1, wherein the at least one imaging engine comprises a broadband light source.

15. The imaging system of claim 14, wherein the at least one imaging engine further comprises a spectrometer-based OCT interferometer for separating different bands of the broadband light within the sample arms.

16. A method of using a multiplexed OCT imaging system to provide a plurality of images, the method comprising:
emitting light from at least one light source upon a plurality of targets, each adjacent to a sample arm, and collecting reflected light from the targets;
emitting reference light from the light source upon a plurality of reference planes, each associated with a reference arm, the reference arm at least partially sharing a common beam path with one of the sample arms with respect to a target;
simultaneously operating the sample arms to generate interference patterns (i) resulting from optical path-length or phase differences between the sample arms and corresponding ones of the reference arms and (ii) encoding spatial dimensions and locations of structures with respect to targets adjacent to the respective sample arms; and
multiplexing optical signals separately representing the interference patterns simultaneously generated by the simultaneously operative sample arm, thereby generating a plurality of OCT images, each image associated with one of the plurality of targets.

17. The method of claim 16, wherein the multiplexing is wavelength-division multiplexing.

18. The method of claim 16, wherein the multiplexing is time-division multiplexing.

\* \* \* \* \*